(12) United States Patent
Smythe et al.

(10) Patent No.: US 9,199,976 B2
(45) Date of Patent: Dec. 1, 2015

(54) HAEMATOPOIETIC-PROSTAGLANDIN D2 SYNTHASE INHIBITORS

(75) Inventors: Mark Leslie Smythe, Bardon (AU); Jack Urquhart Flanagan, Auckland (NZ)

(73) Assignee: The University of Queensland, Brisbane (AU)

( * ) Notice: Subject to any disclaimer, the term of this patent is extended or adjusted under 35 U.S.C. 154(b) by 42 days.

(21) Appl. No.: 13/701,380

(22) PCT Filed: Jun. 1, 2011

(86) PCT No.: PCT/AU2011/000684
§ 371 (c)(1),
(2), (4) Date: Feb. 11, 2013

(87) PCT Pub. No.: WO2011/150457
PCT Pub. Date: Dec. 8, 2011

(65) Prior Publication Data
US 2013/0137684 A1 May 30, 2013

Related U.S. Application Data

(60) Provisional application No. 61/350,296, filed on Jun. 1, 2010.

(51) Int. Cl.
| C07D 409/04 | (2006.01) |
| A61K 31/381 | (2006.01) |
| C07D 409/14 | (2006.01) |
| C07D 471/10 | (2006.01) |
| C07D 413/14 | (2006.01) |

(52) U.S. Cl.
CPC ............ C07D 409/04 (2013.01); A61K 31/381 (2013.01); C07D 409/14 (2013.01); C07D 413/14 (2013.01); C07D 471/10 (2013.01)

(58) Field of Classification Search
CPC ........................... C07D 409/04; A61K 31/381
USPC ......... 544/92; 546/17, 194, 280.4; 514/230.5, 514/278, 318, 336
See application file for complete search history.

(56) References Cited

U.S. PATENT DOCUMENTS

| 5,521,173 | A | 5/1996 | Venkatesan et al. | |
| 5,883,105 | A * | 3/1999 | Anthony ...................... | 514/277 |
| 2003/0195192 | A1 | 10/2003 | Haviv et al. | |
| 2004/0242615 | A1* | 12/2004 | Yamamori et al. ............ | 514/277 |
| 2006/0258672 | A1 | 11/2006 | Barbosa et al. | |
| 2007/0043066 | A1 | 2/2007 | Sum et al. | |
| 2008/0113983 | A1* | 5/2008 | Chapdelaine et al. ..... | 514/233.2 |
| 2008/0167342 | A1* | 7/2008 | Strobel et al. ................. | 514/318 |
| 2010/0016360 | A1 | 1/2010 | Haydar et al. | |
| 2010/0016598 | A1* | 1/2010 | Valacchi et al. ............. | 546/194 |
| 2010/0298298 | A1 | 11/2010 | Clauss et al. | |

FOREIGN PATENT DOCUMENTS

| WO | WO 03/059871 | A1 | 7/2003 |
| WO | WO 2004/006922 | A1 | 1/2004 |
| WO | WO 2006/023462 | A1 | 3/2006 |
| WO | WO 2007/041634 | A1 | 4/2007 |
| WO | WO 2007/061862 | A2 | 5/2007 |
| WO | WO 2007/098352 | A2 | 8/2007 |
| WO | WO 2007/118137 | A1 | 10/2007 |
| WO | WO 2007/119600 | A1 | 10/2007 |
| WO | WO 2008/045564 | * | 4/2008 |
| WO | WO 2008/078196 | A2 | 7/2008 |
| WO | WO 2008/121670 | A1 | 10/2008 |
| WO | WO 2009/077680 | A1 | 6/2009 |
| WO | WO 2009/134668 | A2 | 11/2009 |
| WO | WO 2010/137738 | A1 | 12/2010 |
| WO | WO 2011/029537 | * | 3/2011 |
| WO | WO 2011/106276 | * | 9/2011 |

OTHER PUBLICATIONS

Koehler et al., The Singlet-Triplet Exchange Energy in Conjugated Polymers, Advanced Functional Materials, vol. 14, No. 1, pp. 11-18, Jan. 2004.*
Hille et al., Optimization of the First Selective Steroid-11β-hydroxylase (CYP11B1) Inhibitors for the Treatment of Cortisol Dependent Diseases, ACS Medicinal Chemistry Letters, vol. 2, No. 8, pp. 559-564, Jun. 2011.*
Christ et al., "Development and Characterization of New Inhibitors of the Human and Mouse Hematopoietic Prostaglandin $D_2$ Synthases," J Med Chem 53(15): 5536-5548, 2010.
Patani et al., "Bioisosterism: A Rational Approach in Drug Design," Chem Rev 96(8): 3147-3176, 1996.
International Preliminary Report on Patentability, PCT/AU2011/000684, mailed Dec. 4, 2012, 9 pages.
Hohwy et al., "Novel Prostaglandin D Synthase Inhibitors Generated by Fragment-Based Drug Design," J Med Chem 51: 2178-2186, 2008.
Price et al., "Identification and optimization of a series of substituted 5-pyridin-2-yl-thiophene-2-hydroxamic acids as potent histone deacetylase (HDAC) inhibitors," Bioorganic & Medicinal Chemistry Letters 17: 363-369, 2007.
Van Der Eycken et al., "Synthesis of (E)-5-(2-arylvinyl)-2-(hetero)arylpyridines, (E)-2-(2-arylvinyl)-5-methoxycarbonyl-pyridines and (E,E)-2,5-bis(2-arylvinyl)pyridines as polarity and pH probes," J Chem Soc, Perkin Trans 2: 928-937, 2002.

* cited by examiner

Primary Examiner — Deepak Rao
(74) Attorney, Agent, or Firm — Seed IP Law Group PLLC

(57) ABSTRACT

The present invention generally relates to compounds that inhibit haematopoietic-prostaglandin $D_2$ synthase (H-PGDS), to compositions containing them and to their use in treating or preventing conditions and diseases associated with H-PGDS, such as allergies and inflammation.

11 Claims, 4 Drawing Sheets

HAEMATOPOIETIC-PROSTAGLANDIN D2 SYNTHASE INHIBITORS

FIELD OF THE INVENTION

The present invention generally relates to compounds that inhibit haematopoietic-prostaglandin $D_2$ synthase (H-PGDS), to compositions containing them and to their use in treating or preventing conditions and diseases associated with H-PGDS, such as allergies and inflammation.

BACKGROUND OF THE INVENTION

Bibliographical details of various publications referred to in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many non-steroidal anti-inflammatory drugs, such as aspirin and ibuprofen, act by inhibiting cyclooxygenase, which in turn affects production of various prostaglandins including prostaglandin $H_2$ ($PGH_2$), prostaglandin $D_2$ ($PGD_2$), prostaglandin $E_2$ ($PGE_2$), prostaglandin $F_{2\alpha}$ ($PGF_{2\alpha}$), prostacyclin ($PGI_2$) and thromboxane (TX) $A_2$.

As each prostaglandin has different biological activities, cyclooxygenase inhibition may impact on a number of biological processes with adverse effects. For example, this has been known to include gastric toxicity and cardiovascular complications associated with prostacyclin loss. Consequently, targeting the production of particular prostaglandins downstream of cyclooxygenase provides a much more specific biological effect that avoids such complications.

$PGD_2$ is a major pro-inflammatory mediator of the allergic response and is known to have roles in body temperature regulation, sleep-wake regulation, relaxation of smooth muscle, tactile pain response, bronchoconstriction, and inflammation. It is readily detected in nasal and bronchial lavage fluids of patients with asthma, allergic rhinitis, atopic dermatitis, and allergic conjunctivitis. $PGD_2$ triggers a range of biological effects consistent with a pathological role in asthma and allergy, including airways eosinophilia, obstruction, hypersensitivity and mucus hypersecretion. Compounds that inhibit $PGD_2$ production are therefore attractive targets for drug development.

$PGD_2$ is active in both the central nervous system and peripheral tissues. Production of $PGD_2$ is performed by two genetically distinct $PGD_2$ synthase (PGDS) enzymes: brain-type-PODS (L-PGDS) and haematopoietic-PGDS (H-PGDS). L-PGDS expression in mammals appears to be mostly restricted to the central nervous system, testis and heart. In contrast, $PGD_2$ synthesis in peripheral tissues is likely to be through H-PGDS.

Targeting the inhibition of $PGD_2$ synthesis may allow mediation of pro-inflammatory responses without the side effects of cyclooxygenase inhibition. There is therefore a need for small molecules that inhibit H-PGDS.

SUMMARY OF THE INVENTION

The present invention is predicated in part on the discovery that compounds of formula (I) inhibit H-PGDS. This discovery has been reduced to practice in novel compounds, compositions containing them and in methods for their preparation and use, as described hereinafter.

Some compounds of the present invention advantageously exhibit selectivity for H-PGDS over cyclooxygenases and other prostaglandin synthases.

DETAILED DESCRIPTION OF THE INVENTION

Figure 1:
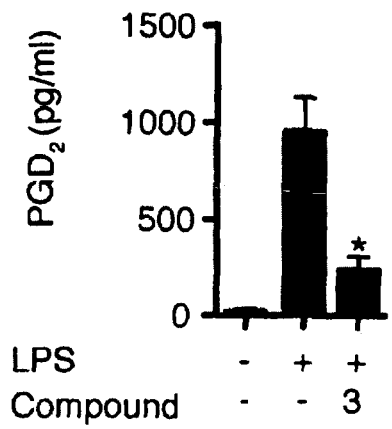
FIG. 1 shows results of H-PGDS inhibitory activity of compound 3 in mouse primary bone marrow-derived macrophages (BMM).
Figure 1:
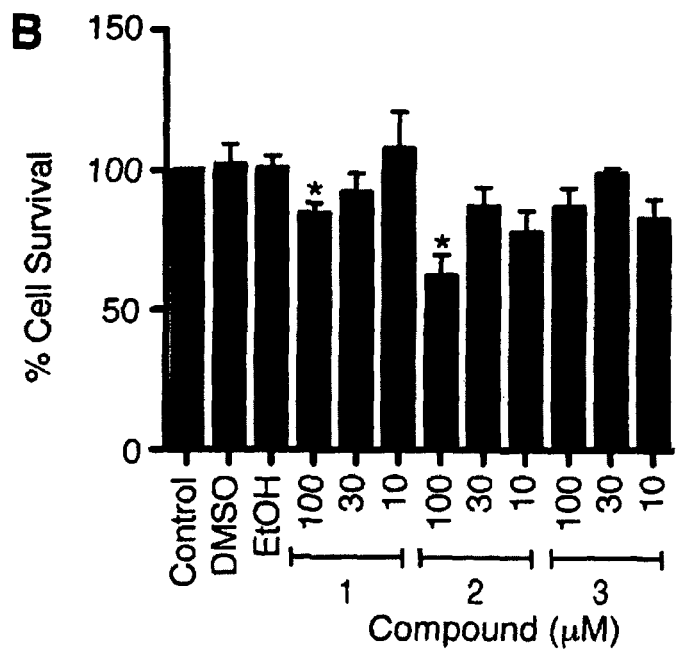

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

In one aspect of the invention, there is provided a method of treating or preventing a haematopoietic-prostaglandin $D_2$ synthase associated disease or condition, comprising administering to a subject an effective amount of a compound of formula (I) or a pharmaceutically acceptable salt thereof:

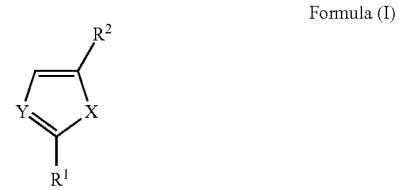

Formula (I)

wherein
Y is —N— or —CH—;
X is —NH—, —O—, —S—, —N=CH— or —CH=N—;
$R^1$ is optionally substituted thienyl or optionally substituted thiazolyl;
$R^2$ is selected from —C(=O)—$NR^3R^4$, —C(=S)—$NR^3R^4$, —$CH_2$—$CHR^5R^6$, —CH=$CR^5R^6$, —C≡$CR^7$, —$CH_2$—$OR^7$, —C(=O)—$OR^7$, —$CH_2$—$NR^3R^4$, —$CH_2$—C(OH)$R^5R^6$, —CH(OH)—C(OH)$R^5R^6$, —C(=O)—NH—$NR^3R^4$, —C(=O)—NH—$OR^7$, —P(=O)(OH)—$NR^3R^4$, —NH—C(=O)—$NR^3R^4$, —O—C(=O)—$NR^3R^4$, —CH($CF_3$)—$NR^3R^4$, and

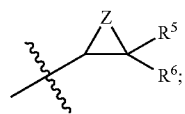

Z is selected from —$CH_2$— or —NH—;
$R^3$ is selected from —$CHR^8R^9$, —$C_{0\text{-}6}$alkyl-$R^{10}$, —$C_{2\text{-}6}$alkenyl-$R^{10}$, and —$C_{2\text{-}6}$alkynyl-$R^{10}$;

R$^4$ is selected from hydrogen, hydroxyl, alkyl, haloalkyl, alkenyl, and alkynyl; or R$^3$ and R$^4$ taken together form a heterocyclyl or heteroaryl ring;

R$^5$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;

R$^6$ is selected from hydrogen, hydroxyl, alkyl, alkenyl, and alkynyl; or R$^5$ and R$^6$ taken together form a cycloalkyl, cycloalkenyl, aryl, heterocyclyl or heteroaryl ring;

R$^7$ is selected from —CHR$^8$R$^9$, —C$_{0-6}$alkyl-R$^{10}$, —C$_{2-6}$alkenyl-R$^{10}$, and C$_{2-6}$alkynyl-R$^{10}$;

R$^8$ is selected from —CO$_2$H, —CONH$_2$, —CONR$^{16}$—CHR$^{17}$—CONH$_2$, —CONR$^{16}$—CHR$^{17}$—CO$_2$H, cycloalkyl, cycloalkenyl, aryl, heterocyclyl, heteroaryl, —C$_{1-6}$alkylR$^{10}$, —C$_{2-6}$alkenylR$^{10}$ and C$_{2-6}$alkynylR$^{10}$;

R$^9$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;

R$^{10}$ is selected from cycloalkyl, cycloalkenyl, aryl, heterocyclyl and heteroaryl;

R$^{16}$ is selected from hydrogen, hydroxyl, alkyl, haloalkyl, alkenyl, and alkynyl; and R$^{17}$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;

wherein each alkyl, alkenyl, alkynyl, cycloalkyl, cycloalkenyl, aryl, heterocyclyl and heteroaryl are optionally substituted with one or more optional substituents.

In one embodiment, the compound of formula (I) is a compound of formula (II) or a pharmaceutically acceptable salt thereof:

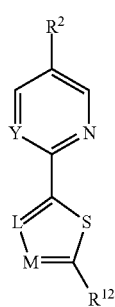

Formula (II)

wherein
Y is —N— or —CH—;
L and M are independently selected from N and CR$^{13}$, provided that both L and M are not N;
R$^2$ is selected from —C(=O)—NR$^3$R$^4$, —C(=S)—NR$^3$R$^4$, —CH$_2$—CHR$^5$R$^6$, —CH=CR$^5$R$^6$, —C≡CR$^7$, —CH$_2$—OR$^7$, —C(=O)—OR$^7$, —CH$_2$—NR$^3$R$^4$, —CH$_2$—C(OH)R$^5$R$^6$, —CH(OH)—C(OH)R$^5$R$^6$, —C(=O)—NH—NR$^3$R$^4$, —C(=O)—NH—OR$^7$, —P(=O)(OH)—NR$^3$R$^4$, —NH—C(=O)—NR$^3$R$^4$, —O—C(=O)—NR$^3$R$^4$, —CH(CF$_3$)—NR$^3$R$^4$, and

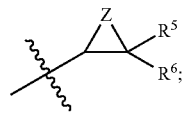

Z is selected from —CH$_2$— or —NH—;
R$^3$ is selected from —CHR$^8$R$^{11}$, —C$_{2-6}$alkenyl-R$^{10}$, and —C$_{2-6}$alkynyl-R$^{10}$;

R$^4$ is selected from hydrogen, hydroxyl, alkyl, haloalkyl, alkenyl, and alkynyl; or R$^3$ and R$^4$ taken together form a heterocyclyl or heteroaryl ring;

R$^5$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;

R$^6$ is selected from hydrogen, hydroxyl, alkyl, alkenyl, and alkynyl; or R$^5$ and R$^6$ taken together form a cycloalkyl, cycloalkenyl, aryl, heterocyclyl or heteroaryl ring;

R$^7$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;

R$^8$ is selected from —CO$_2$H, —CONH$_2$, —CONR$^{16}$—CHR$^{17}$—CONH$_2$, —CONR$^{16}$—CHR$^{17}$—CO$_2$H, cycloalkyl, cycloalkenyl, aryl, heterocyclyl, heteroaryl, —C$_{1-6}$alkylR$^{10}$, —C$_{2-6}$alkenylR$^{10}$ and —C$_{2-6}$alkynylR$^{10}$;

R$^9$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;

R$^{10}$ is selected from cycloalkyl, cycloalkenyl, aryl, heterocyclyl and heteroaryl;

R$^{11}$ is selected from —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;

R$^{12}$ and R$^{13}$ are independently selected from hydrogen, cyano, nitro, halo, —C$_{1-6}$alkyl, —C$_{2-6}$alkenyl, —C$_{0-6}$alkylaryl, —C$_{0-6}$alkylheteroaryl, —C$_{0-6}$alkylcycloalkyl, —C$_{0-6}$alkylcycloalkenyl, —C$_{0-6}$alkylheterocyclyl, —O—R$^{14}$, —C(=O)—R$^{14}$, —C(=O)—O—R$^{14}$, —O—C(=O)—R$^{14}$, —S(O)$_t$—R$^{14}$, —N(R$^{14}$)$_2$, and —C(=O)—N(R$^{14}$)$_2$, wherein each R$^{14}$ is independently selected from H, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl or —C$_{0-6}$alkylheterocyclyl;

t is 0-2;

R$^{16}$ is selected from hydrogen, hydroxyl, alkyl, haloalkyl, alkenyl, and alkynyl; and R$^{17}$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;

wherein each alkyl, alkenyl, alkynyl, cycloalkyl, cycloalkenyl, aryl, heterocyclyl and heteroaryl are optionally substituted with one or more optional substituents.

In one embodiment, the compound of formula (I) is a compound of formula (III) or a pharmaceutically acceptable salt thereof:

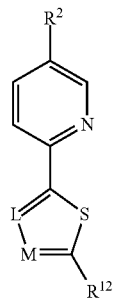

Formula (III)

wherein
L and M are independently selected from N and CR$^{13}$, provided that both L and M are not N;
R$^2$ is selected from —C(=O)—NR$^3$R$^4$, —C(=S)—NR$^3$R$^4$, —CH$_2$—CHR$^5$R$^6$, —CH=CR$^5$R$^6$, —C≡CR$^7$, —CH$_2$—OR$^7$, —C(=O)—OR$^7$, —CH$_2$—NR$^3$R$^4$, —CH$_2$—C(OH)R$^5$R$^6$, —CH(OH)—C(OH)R$^5$R$^6$, —C(=O)—NH—NR$^3$R$^4$, —C(=O)—NH—OR$^7$, —P(=O)(OH)—NR$^3$R$^4$, —NH—C(=O)—NR$^3$R$^4$, —CH(CF$_3$)—NR$^3$R$^4$, and

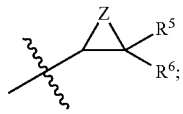

Z is selected from —CH$_2$— or —NH—;
R$^3$ is selected from —CHR$^8$R$^{11}$, —C$_{2-6}$alkyl-R$^{10}$, —C$_{2-6}$alkenyl-R$^{10}$, and —C$_{2-6}$alkynyl-R$^{10}$;
R$^4$ is selected from hydrogen, hydroxyl, alkyl, haloalkyl, alkenyl, and alkynyl; or R$^3$ and R$^4$ taken together form a heterocyclyl or heteroaryl ring;
R$^5$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;
R$^6$ is selected from hydrogen, hydroxyl, alkyl, alkenyl, and alkynyl; or R$^5$ and R$^6$ taken together form a cycloalkyl, cycloalkenyl, aryl, heterocyclyl or heteroaryl ring;
R$^7$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;
R$^8$ is selected from —CO$_2$H, —CONH$_2$, —CONR$^{16}$—CHR$^{17}$—CONH$_2$, —CONR$^{16}$—CHR$^{17}$—CO$_2$H, cycloalkyl, cycloalkenyl, aryl, heterocyclyl, heteroaryl, —C$_{1-6}$alkylR$^{10}$, —C$_{2-6}$alkenylR$^{10}$ and —C$_{2-6}$alkynylR$^{10}$;
R$^9$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;
R$^{10}$ is selected from cycloalkyl, cycloalkenyl, aryl, heterocyclyl and heteroaryl;
R$^{11}$ is selected from —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;
R$^{12}$ and R$^{13}$ are independently selected from hydrogen, cyano, nitro, halo, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl, —C$_{0-6}$alkylheterocyclyl, —O—R$^{14}$, —C(=O)—R$^{14}$, —C(=O)—O—R$^{14}$, —O—C(=O)—R$^{14}$, —S(O)$_t$—R$^{14}$, —N(R$^{14}$)$_2$, and —C(=O)—N(R$^{14}$)$_2$, wherein each R$^{14}$ is independently selected from H, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl or —C$_{0-6}$alkylheterocyclyl;
t is 0-2;
R$^{16}$ is selected from hydrogen, hydroxyl, alkyl, haloalkyl, alkenyl, and alkynyl; and
R$^{17}$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;
wherein each alkyl, alkenyl, alkynyl, cycloalkyl, cycloalkenyl, aryl, heterocyclyl and heteroaryl are optionally substituted with one or more optional substituents.

In some embodiments of formula (I), (II) or (III), one or more of the following applies:
X is

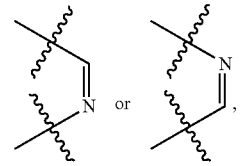

especially

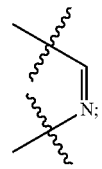 [SMILES: */C=N\*]

Y is CH;
R$^1$ is optionally substituted thienyl, especially unsubstituted thienyl or thienyl substituted with groups independently selected from cyano, nitro, halo, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl, —C$_{0-6}$alkylheterocyclyl, —O—R$^{14}$, —C(=O)—R$^{14}$, —C(=O)—O—R$^{14}$, —O—C(=O)—R$^{14}$, —S(O)$_t$—R$^{14}$, —N(R$^{14}$)$_2$, and —C(=O)—N(R$^{14}$)$_2$, wherein t is 0-2; especially unsubstituted thienyl or thienyl substituted with cyano, nitro, halo, —C$_{1-6}$alkyl, —C$_{2-6}$alkenyl, —C$_{2-6}$alkynyl, —C(=O)—R$^{14}$, —C(=O)—O—R$^{14}$, —O—C(=O)—R$^{14}$, —N(R$^{14}$)$_2$, or —C(=O)—N(R$^{14}$)$_2$; more especially unsubstituted thienyl or thienyl substituted with —C(=O)—R$^{14}$, —C(=O)—O—R$^{14}$, —O—C (=O)—R$^{14}$, —N(R$^{14}$)$_2$, or —C(=O)—N(R$^{14}$)$_2$; most especially unsubstituted thienyl;

each R$^{14}$ is independently selected from H, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl or —C$_{0-6}$alkylheterocyclyl, especially H or —C$_{1-6}$alkyl;

L and M are both CR$^{13}$;

R$^{12}$ and R$^{13}$ are independently selected from hydrogen cyano, nitro, halo, —C$_{1-6}$alkyl, —C$_{2-6}$alkenyl, —C$_{2-6}$alkynyl, —C(=O)—R$^{14}$, —C(=O)—O—R$^{14}$, —O—C(=O)—R$^{14}$, —N(R$^{14}$)$_2$, and —C(=O)—N(R$^{14}$)$_2$; especially —C(=O)—R$^{14}$, —C(=O)—O—R$^{14}$, —O—C(=O)—R$^{14}$, —N(R$^{14}$)$_2$, and —C(=O)—N(R$^{14}$)$_2$; more especially hydrogen;

R$^{12}$ is hydrogen and L and M are both CH;

R$^2$ is selected from —C(=O)—NR$^3$R$^4$, —C(=S)—NR$^3$R$^4$, —CH=CR$^5$R$^6$, —CH$_2$—OR$^7$, —C(=O)—OR$^7$, —CH$_2$—NR$^3$R$^4$, —C(=O)—NH—NR$^3$R$^4$, —C(=O)—NH—OR$^7$, —NH—C(=O)—NR$^3$R$^4$, —O—C(=O)—NR$^3$R$^4$ and —CH(CF$_3$)—NR$^3$R$^4$, especially —C(=O)—NR$^3$R$^4$, —CH$_2$—OR$^7$, —CH$_2$—NR$^3$R$^4$, —NH—C(=O)—NR$^3$R$^4$, —CH=CR$^5$R$^6$ and —CH(CF$_3$)—NR$^3$R$^4$, more especially —C(=O)—NR$^3$R$^4$ or —CH(CF$_3$)—NR$^3$R$^4$, most especially —C(=O)—NR$^3$R$^4$;

R$^3$ is selected from —CHR$^8$R$^9$, —CHR$^8$R$^{11}$ or —C$_{0-6}$alkyl-R$^{10}$; especially —CHR$^8$R$^9$, —CHR$^8$R$^{11}$ or —C$_{1-6}$alkyl-R$^{10}$; more especially —CHR$^8$R$^{11}$ or —C$_{2-6}$alkyl-R$^{10}$; most especially —CHR$^8$R$^{11}$;

R$^4$ is hydrogen, alkyl, haloalkyl or perfluoroalkyl; especially hydrogen;

R$^3$ and R$^4$ taken together form a heterocyclyl or heteroaryl ring; especially where R$^3$ and R$^4$ form a monocyclic heterocyclyl or heteroaryl ring which is substituted by a cycloalkyl, cycloalkenyl, aryl, heterocyclyl or heteroaryl group, or where R$^3$ and R$^4$ form a bicyclic heterocyclyl or heteroaryl ring, or where R$^3$ and R$^4$ form a tricyclic spirane heterocyclyl group; more especially R$^3$ and R$^4$ together form 1,2,3,4-tetrahydroisoquinolinyl,

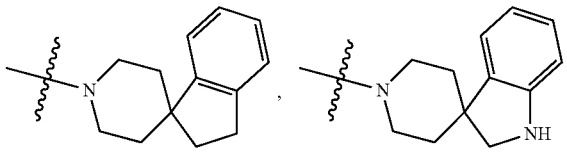 [SMILES: *N1CCC2(CCc3ccccc32)CC1 ; *N1CCC2(CC1)CNc1ccccc12]

which is optionally substituted at the ring nitrogen with a —SO$_2$Me group, or piperidinyl which is substituted with benzimidazol-2-one or 1,3-benzoxazin-2-one;

R$^5$ is selected from —CHR$^8$R$^9$, —CHR$^8$R$^{11}$ or —C$_{0-6}$alkyl-R$^{10}$; especially —CHR$^8$R$^9$, —CHR$^8$R$^{11}$ or —C$_{1-6}$alkyl-R$^{10}$; more especially —CHR$^8$R$^{11}$ or —C$_{2-6}$alkyl-R$^{10}$; most especially —CHR$^8$R$^{11}$;

R$^6$ is hydrogen, alkyl or haloalkyl; especially hydrogen;

R$^5$ and R$^6$ taken together form a heterocyclyl or heteroaryl ring;

R$^7$ is selected from —CHR$^8$R$^9$, —CHR$^8$R$^{11}$ or —C$_{0-6}$alkyl-R$^{10}$; especially —CHR$^8$R$^9$, —CHR$^8$R$^{11}$ or —C$_{1-6}$alkyl-R$^{10}$; more especially —CHR$^8$R$^{11}$ or —C$_{2-6}$alkyl-R$^{10}$; most especially —CHR$^8$R$^{11}$;

R$^8$ is selected from —CO$_2$H, —CONH$_2$, cycloalkyl, cycloalkenyl, aryl, heterocyclyl, heteroaryl, —C$_{1-6}$alkylR$^{10}$, —C$_{2-6}$alkenylR$^{10}$ and —C$_{2-6}$alkynylR$^{10}$; especially —CONH$_2$, aryl, heterocyclyl, heteroaryl, —C$_{1-6}$alkylR$^{10}$, —C$_{2-6}$alkenylR$^{10}$ and —C$_{2-6}$alkynylR$^{10}$; more especially —CONH$_2$, aryl and —C$_{1-6}$alkylR$^{10}$; more especially —CONH$_2$ and aryl; most especially naphthyl, —CONH$_2$ and phenyl, R$^9$ is selected from —C$_{1-6}$alkyl, —C$_{1-6}$ perfluoroalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$ perfluoroalkyl, —C$_{0-6}$alkylOH, —C$_{0-6}$alkylNH$_2$, —C$_{0-6}$alkylSH, —C$_{0-6}$alkylSC$_{1-6}$alkyl, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$ perfluoroalkyl or —C$_{0-6}$alkylaryl; more especially C$_1$alkylaryl, aryl, methyl or —CF$_3$; most especially —CH$_2$-phenyl, phenyl, methyl or —CF$_3$;

R$^{11}$ is selected from —C$_{1-6}$alkyl, —C$_{1-6}$ perfluoroalkyl, —C$_{0-6}$alkylOH, —C$_{0-6}$alkylNH$_2$, —C$_{0-6}$alkylSH, —C$_{0-6}$alkylSC$_{1-6}$alkyl, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$ perfluoroalkyl or —C$_{0-6}$alkylaryl; more especially C$_1$alkylaryl, aryl, methyl or —CF$_3$; most especially —CH$_2$-phenyl, phenyl, methyl or —CF$_3$;

R$^{16}$ is selected from hydrogen, alkyl, haloalkyl or perfluoroalkyl; especially hydrogen;

R$^{17}$ is selected from hydrogen, —C$_{1-6}$alkyl, —C$_{1-6}$haloalkyl, —C$_{0-6}$alkylOH, —C$_{0-6}$alkylSH, —C$_{0-6}$alkylSC$_{1-6}$alkyl, —C$_{0-6}$alkylcycloalkyl; more especially hydrogen, —C$_{1-6}$alkyl, —C$_{1-6}$ perfluoroalkyl, —C$_{0-6}$alkylcycloalkyl; most especially methyl or —CF$_3$;

wherein each alkyl, alkenyl, alkynyl, cycloalkyl, cycloalkenyl, aryl, heterocyclyl and heteroaryl are optionally substituted with one or more optional substituents.

In another aspect of the invention there is provided a use of a compound of formula (I), (II) or (III) in the manufacture of a medicament for the treatment or prevention of a disease or condition associated with inhibition of H-PGDS.

Reference herein to "treatment" and "prevention" is to be considered in its broadest context. The term "treatment" does not necessarily imply that a subject is treated until total recovery. Similarly, "prevention" does not necessarily mean that the subject will not eventually contract a disease or condition. Accordingly, "treatment" includes amelioration of the symptoms of a particular disease or condition, or reducing the severity of an existing disease, or condition. "Prevention" may be considered as reducing the likelihood of onset of a particular disease or condition or preventing or otherwise reducing the risk of developing a particular disease or condition.

An effective amount of a compound of formula (I) means an amount necessary at least partly to attain the desired response, or to delay the onset or inhibit progression or halt altogether, the onset or progression of a particular disease or condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. In one embodiment, the dosage is in the range of 1 µg to 1 g per kg of body weight per dosage, such as in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

The term "subject" as used herein includes mammals, humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). In some embodiments, the subject is human or a laboratory test animal, especially a human.

As used herein, "an H-PGDS associated disease or condition" is a disease or condition which benefits from the inhibition of H-PGDS. For example, such diseases or conditions are those in which H-PGDS is inappropriately stimulated or overactive. H-PGDS associated diseases or conditions include allergies, inflammation, pain, bronchoconstriction, muscle necrosis, cancer, arthritis, irritable bowel diseases, irritable bowel syndrome, skin inflammation and irritation, and cardiovascular diseases or conditions. In one embodiment, the H-PGDS associated diseases or conditions are selected from cancer, rheumatoid arthritis, Crohn's disease, ulcerative colitis, painful diabetic neuropathy, postherpetic neuralgia, eczema, psoriasis, chronic pain, chronic inflammation, neuropathic pain conditions, niacin-induced skin flushing and celiac type disease (for example resulting from lactose intolerance), carpal tunnel syndrome, back pain, headache, cancer pain, arthritic pain, chronic post-surgical pain, allergic conjunctivitis, atopic dermatitis, neuroinflammation, allergic rhinitis, nasal congestion, rhinorrhea, perennial rhinitis, nasal inflammation, asthma, chronic obstructive pulmonary disease (COPD), chronic or acute bronchoconstriction, chronic bronchitis, small airways obstruction, emphysema, chronic eosinophilic pneumonia, adult respiratory distress syndrome, airways disease that is associated with pulmonary hypertension, acute lung injury, bronchiectasis, sinusitis, allergic conjunctivitis, atopic dermatitis, and airways eosinophilia, obstruction, hypersensitivity or hypersecretion. In one embodiment, these diseases or conditions include allergies, inflammation and chronic pain conditions. For example, in one embodiment, the disease or condition is asthma, allergic conjunctivitis, atopic dermatitis, allergic rhinitis, neuroinflammation, chronic obstructive pulmonary disease or airways eosinophilia, obstruction, hypersensitivity or hypersecretion.

In some embodiments, compounds of the invention advantageously display selectivity for H-PGDS over other prostaglandin synthases. This advantageously may provide compounds that provide fewer side effects than other pharmaceuticals that target prostaglandin production.

In a further aspect of the invention there is provided a method of inhibiting H-PGDS, comprising contacting H-PGDS with a compound of formula (I). It should be understood that the method in this aspect of the invention relates to H-PGDS which may be located in vitro or in vivo, especially in vitro. This method includes, but is not limited to, screening of compound libraries to identify compounds that bind to H-PGDS, assays to determine the biological activity of compounds that bind to H-PGDS, experiments to develop a pharmacophore of H-PGDS or experiments to investigate the physiology or pharmacology of H-PGDS.

The present invention further contemplates a combination of therapies, such as the administration to a subject of the compounds of the invention or pharmaceutically acceptable salts or prodrugs thereof, together with other agents or procedures which are useful in the treatment or prevention of diseases and conditions in respect of which inhibition of H-PGDS is associated with effective treatment.

The compounds of formula (I), (II) or (III) or pharmaceutically acceptable salts or prodrugs thereof may also be administered in combination with other agents or procedures which are useful in the treatment or prevention of H-PGDS associated diseases or conditions. For example, other agents that may be used with compounds of formula (I), (II) or (III) include anti-inflammatories such as corticosteroids (for example, fluticasone, budesonide and mometasone), especially oral or intranasal anti-inflammatories; bronchodilators such as anticholinergics (for example, tiotropium bromide and ipratropin) and $\beta_2$ agonists (for example, salmeterol, salbutamol, camoterol, indacaterol and formaterol); methylxanthines such as theophylline; and biologics, such as monoclonal antibodies (for example antibodies against TNFa and immunoglobulins (eg IgE), including omalizumab). Such combinations may be useful in the treatment of asthma and chronic obstructive pulmonary disease.

Similarly anti-inflammatories such as corticosteroids (for example, fluticasone, budesonide and mometasone), especially oral or intranasal anti-inflammatories; anti-histamines, such as H1-receptor antagonists; oral or intranasal decongestants; and allergan immunotherapy using recombinant allergans such as different types of pollen may be used with compounds of formula (I), (II) and (III), especially for the treatment of allergic rhinitis.

Other agents that may be used with compounds of formula (I), (II) and (III) include glucocorticosteroids or dissociated agonists of the corticoid receptor; $\beta_2$ agonists including long acting $\beta_2$ agonists; muscarinic M3 receptor antagonists or anticholinergic agents; histamine receptor antagonists including H1 or H3 antagonists; 5-lypoxygenase inhibitors; thromboxane inhibitors; 5-lipoxygenase activating protein (FLAP) antagonists; leukotriene antagonists including antagonists of $LTB_4$, $LTC_4$, $LTD_4$ and $LTE_4$; $\alpha_1$- and $\alpha_2$-adrenoceptor agonist vasoconstrictor sympathomimetic agents for decongestant use; PDE inhibitors including PDE3, PDE4 and PDE5 inhibitors such as theophylline; sodium cromoglycate; monoclonal antibodies active against endogenous inflammatory entities; integrin antagonists; adhesion molecule inhibitors such as VLA-4 antagonists; kinin-$B_1$- or $B_2$-receptor antagonists; immunosuppressive agents, including inhibitors of the IgE pathway and cyclosporin; inhibitors of matrix metalloproteases (MMPs) such as MMP9 and MMP12; tachykinin NK1, NK2 or NK3 receptor antagonists; protease inhibitors such as elastase inhibitors, chymase and cathepsin G; adenosine Ata receptor agonists and A2b antagonists; inhibitors of urokinase; compounds that act on dopamine receptors such as D2 agonists; modulators of the NFκB pathway such as IKK inhibitors; modulators of cytokine signalling pathways such as syk kinase, JAK kinase, p38 kinase, SPHK-1 kinase, Rho kinase, EGF-R or MK-2; agents that can be classed as mucolytics or anti-tussive, and mucokinetics; antibiotics; antivirals; vaccines; chemokines; epithelial sodium channel (ENaC) blockers or epithelial sodium channel (ENaC) inhibitors; P2Y2 agonists and other nucleotide receptor agonists; niacin; and adhesion factors including VLAM, ICAM and ELAM.

In another aspect the present invention relates to a compound of formula (II):

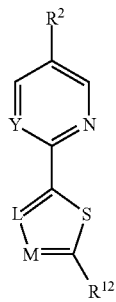

Formula (II)

wherein
Y is —N— or —CH—;
L and M are independently selected from N and CR$^{13}$, provided that both L and M are not N;
R$^2$ is selected from —C(=O)—NR$^3$R$^4$, —C(=S)—NR$^3$R$^4$, —CH$_2$—CHR$^5$R$^6$, —CH=CR$^5$R$^6$, —C≡CR$^7$, —CH$_2$—OR$^7$, —C(=O)—OR$^7$, —CH$_2$—NR$^3$R$^4$, —CH$_2$—C(OH)R$^5$R$^6$, —CH(OH)—C(OH)R$^5$R$^6$, —C(=O)—NH—NR$^3$R$^4$, —C(=O)—NH—OR$^7$, —P(=O)(OH)—NR$^3$R$^4$, —NH—C(=O)—NR$^3$R$^4$, —O—C(=O)—NR$^3$R$^4$, —CH(CF$_3$)—NR$^3$R$^4$, and

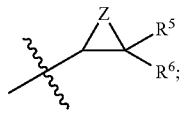

Z is selected from —CH$_2$— or —NH—;
R$^3$ is selected from —CHR$^8$R$^{11}$, —C$_{2-6}$alkyl-R$^{10}$, —C$_{2-6}$alkenyl-R$^{10}$, and —C$_{2-6}$alkynyl-R$^{10}$;
R$^4$ is selected from hydrogen, hydroxyl, alkyl, haloalkyl, alkenyl, and alkynyl; or R$^3$ and R$^4$ taken together form a heterocyclyl or heteroaryl ring;
R$^5$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;
R$^6$ is selected from hydrogen, hydroxyl, alkyl, alkenyl, and alkynyl; or R$^5$ and R$^6$ taken together form a cycloalkyl, cycloalkenyl, aryl, heterocyclyl or heteroaryl ring;
R$^7$ is selected from —CHR$^8$R$^9$, —C$_{0-6}$alkyl-R$^{10}$, —C$_{2-6}$alkenyl-R$^{10}$, and —C$_{2-6}$alkynyl-R$^{10}$;
R$^8$ is selected from —CO$_2$H, —CONH$_2$, —CONR$^{16}$—CHR$^{17}$—CONH$_2$, —CONR$^{16}$—CHR$^{17}$—CO$_2$H, cycloalkyl, cycloalkenyl, aryl, heterocyclyl, heteroaryl, —C$_{1-6}$alkylR$^{10}$, —C$_{2-6}$alkenylR$^{10}$ and —C$_{2-6}$alkynylR$^{10}$;
R$^9$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;
R$^{10}$ is selected from cycloalkyl, cycloalkenyl, aryl, heterocyclyl and heteroaryl;
R$^{11}$ is selected from —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl;
R$^{12}$ and R$^{13}$ are independently selected from hydrogen, cyano, nitro, halo, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl, —C$_{0-6}$alkylheterocyclyl, —O—R$^{14}$, —C(=O)—R$^{14}$, —C(=O)—O—R$^{14}$, —O—C(=O)—R$^{14}$, —S(O)$_t$—R$^{14}$, —N(R$^{14}$)$_2$, and —C(=O)—N(R$^{14}$)$_2$, wherein each R$^{14}$ is independently selected from H, —C$_{1-6}$alkyl, —C$_{2-6}$alkenyl, —C$_{2-6}$alkynyl, —C$_{0-6}$alkylaryl, —C$_{0-6}$alkylheteroaryl, —C$_{0-6}$alkylcycloalkyl, —C$_{0-6}$alkylcycloalkenyl or —C$_{0-6}$alkylheterocyclyl;
t is 0-2;
R$^{16}$ is selected from hydrogen, hydroxyl, alkyl, haloalkyl, alkenyl, and alkynyl; and
R$^{17}$ is selected from hydrogen, —C$_{1-6}$alkyl, —C$_{1-6}$haloalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and C$_{0-6}$alkylheteroaryl;
wherein each alkyl, alkenyl, alkynyl, cycloalkyl, cycloalkenyl, aryl, heterocyclyl and heteroaryl are optionally substituted with one or more optional substituents;
or a salt thereof;
with the provisos that when:
(i) Y is —CH—, R$^2$ is —C(=O)—NR$^3$R$^4$, R$^3$ and R$^4$ taken together form 4-(2-pyrimidinyl)-1-piperazinyl, L is CH and M is CR$^{13}$, then R$^{13}$ is not hydrogen when R$^{12}$ is methyl, and R$^{12}$ is not hydrogen when R$^{13}$ is methyl;
(ii) Y is CH—, R$^2$ is —C(=O)—NR$^3$R$^4$, R$^{12}$ is hydrogen, L is CH and M is CH, then R$^3$ and R$^4$ taken together do not form 5H-pyrrolo[2,1-c][1,4]benzodiazepin-10(11H)-yl, 2-(1-pyrrolidinylmethyl)-1-pyrrolidinyl or 2-methyl-1-pyrrolidinyl; and
(iii) Y is —CH—, R$^2$ is —C(=O)—NR$^3$R$^4$, R$^3$ is 4-[4-(5,6,7,8-tetrahydro-1-methoxy-2-naphthalenyl)-1-piperidinyl]butyl, R$^4$ is hydrogen, and L and M are CH, then R$^{12}$ is not cyano or chloro.

In another aspect the present invention relates to a compound of formula (III):

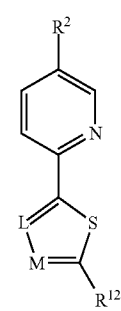

Formula (III)

wherein
L and M are independently selected from N and CR$^{13}$, provided that both L and M are not N;

$R^2$ is selected from —C(=O)—$NR^3R^4$, —C(=S)—$NR^3R^4$, —$CH_2$—$CHR^5R^6$, —CH=$CR^5R^6$, —C≡$CR^7$, —$CH_2$—$OR^7$, —C(=O)—$OR^7$, —$CH_2$—$NR^3R^4$, —$CH_2$—C(OH)$R^5R^6$, —CH(OH)—C(OH)$R^5R^6$, —C(=O)—NH—$NR^3R^4$, —C(=O)—NH—$OR^7$, —P(=O)(OH)—$NR^3R^4$, —NH—C(=O)—$NR^3R^4$, —O—C(=O)—$NR^3R^4$, —CH($CF_3$)—$NR^3R^4$, and

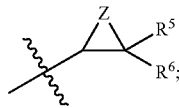

Z is selected from —$CH_2$— or —NH—;

$R^3$ is selected from —$CHR^8R^{11}$, —$C_{2-6}$alkyl-$R^{10}$, —$C_{2-6}$alkenyl-$R^{10}$, and —$C_{2-6}$alkynyl-$R^{10}$;

$R^4$ is selected from hydrogen, hydroxyl, alkyl, haloalkyl, alkenyl, and alkynyl; or $R^3$ and $R^4$ taken together form a heterocyclyl or heteroaryl ring;

$R^5$ is selected from —$CHR^8R^9$, —$C_{2-6}$alkenyl-$R^{10}$, and $C_{2-6}$alkynyl-$R^{10}$;

$R^6$ is selected from hydrogen, hydroxyl, alkyl, alkenyl, and alkynyl; or $R^5$ and $R^6$ taken together form a cycloalkyl, cycloalkenyl, aryl, heterocyclyl or heteroaryl ring;

$R^7$ is selected from —$CHR^8R^9$, —$C_{0-6}$alkyl-$R^{10}$, —$C_{2-6}$alkenyl-$R^{10}$, and —$C_{2-6}$alkynyl-$R^{10}$;

$R^8$ is selected from —$CO_2H$, —$CONH_2$, —$CONR^{16}$—$CHR^{17}$—$CONH_2$, —$CONR^{16}$—$CHR^{17}$—$CO_2H$, cycloalkyl, cycloalkenyl, aryl, heterocyclyl, heteroaryl, —$C_{1-6}$alkyl$R^{10}$, —$C_{2-6}$alkenyl$R^{10}$ and —$C_{2-6}$alkynyl$R^{10}$;

$R^9$ is selected from hydrogen, —$C_{1-6}$alkyl, —$C_{1-6}$haloalkyl, —$C_{2-6}$alkenyl, —$C_{2-6}$alkynyl, —$C_{0-6}$alkylOH, —$C_{0-6}$alkyl$CO_2H$, —$C_{0-6}$alkyl$CONH_2$, —$C_{0-6}$alkyl$NH_2$, —$C_{0-6}$alkylSH, —$C_{0-6}$alkylS$C_{1-6}$alkyl, —$C_{0-6}$alkylNHC(=NH)$NH_2$, —$C_{0-6}$alkylcycloalkyl, —$C_{0-6}$alkylaryl, —$C_{0-6}$alkylheterocyclyl and —$C_{0-6}$alkylheteroaryl;

$R^{10}$ is selected from cycloalkyl, cycloalkenyl, aryl, heterocyclyl and heteroaryl;

$R^{11}$ is selected from —$C_{1-6}$alkyl, —$C_{1-6}$haloalkyl, —$C_{2-6}$alkenyl, —$C_{2-6}$alkynyl, —$C_{0-6}$alkylOH, —$C_{0-6}$alkyl$CO_2H$, —$C_{0-6}$alkyl$CONH_2$, —$C_{0-6}$alkyl$NH_2$, —$C_{0-6}$alkylSH, —$C_{0-6}$alkylS$C_{1-6}$alkyl, —$C_{0-6}$alkylNHC(=NH)$NH_2$, —$C_{0-6}$alkylcycloalkyl, —$C_{0-6}$alkylaryl, —$C_{0-6}$alkylheterocyclyl and —$C_{0-6}$alkylheteroaryl;

$R^{12}$ and $R^{13}$ are independently selected from hydrogen, cyano, nitro, halo, —$C_{1-6}$alkyl, —$C_{2-6}$alkenyl, —$C_{2-6}$alkynyl, —$C_{0-6}$alkylaryl, —$C_{0-6}$alkylheteroaryl, —$C_{0-6}$alkylcycloalkyl, —$C_{0-6}$alkylcycloalkenyl, —$C_{0-6}$alkylheterocyclyl, —O—$R^{14}$, —C(=O)—$R^{14}$, —C(=O)—O—$R^{14}$, —O—C(=O)—$R^{14}$, —S(O)$_t$—$R^{14}$, —N($R^{14}$)$_2$, and —C(=O)—N($R^{14}$)$_2$, wherein each $R^{14}$ is independently selected from H, —$C_{1-6}$alkyl, —$C_{2-6}$alkenyl, —$C_{2-6}$alkynyl, —$C_{0-6}$alkylaryl, —$C_{0-6}$alkylheteroaryl, —$C_{0-6}$alkylcycloalkyl, —$C_{0-6}$alkylcycloalkenyl or —$C_{0-6}$alkylheterocyclyl;

t is 0-2;

$R^{16}$ is selected from hydrogen, hydroxyl, alkyl, haloalkyl, alkenyl, and alkynyl; and $R^{17}$ is selected from hydrogen, —$C_{1-6}$alkyl, —$C_{1-6}$haloalkyl, —$C_{2-6}$alkenyl, —$C_{2-6}$alkynyl, —$C_{0-6}$alkylOH, —$C_{0-6}$alkyl$CO_2H$, —$C_{0-6}$alkyl$CONH_2$, —$C_{0-6}$alkyl$NH_2$, —$C_{0-6}$alkylSH, —$C_{0-6}$alkylS$C_{1-6}$alkyl, —$C_{0-6}$alkylNHC(=NH)$NH_2$, —$C_{0-6}$alkylcycloalkyl, —$C_{0-6}$alkylaryl, —$C_{0-6}$alkylheterocyclyl and —$C_{0-6}$alkylheteroaryl;

wherein each alkyl, alkenyl, alkynyl, cycloalkyl, cycloalkenyl, aryl, heterocyclyl and heteroaryl are optionally substituted with one or more optional substituents;

or a salt thereof;

with the provisos that when:

(i) $R^2$ is —C(=O)—$NR^3R^4$, $R^3$ and $R^4$ taken together form 4-(2-pyrimidinyl)-1-piperazinyl, L is CH and M is $CR^{13}$, then $R^{13}$ is not hydrogen when $R^{12}$ is methyl, and $R^{12}$ is not hydrogen when $R^{13}$ is methyl;

(ii) $R^2$ is —C(=O)—$NR^3R^4$, $R^{12}$ is hydrogen, L is CH and M is CH, then $R^3$ and $R^4$ taken together do not form 5H-pyrrolo[2,1-c][1,4]benzodiazepin-10(11H)-yl, 2-(1-pyrrolidinylmethyl)-1-pyrrolidinyl or 2-methyl-1-pyrrolidinyl; and (iii) $R^2$ is —C(=O)—$NR^3R^4$, $R^3$ is 4-[4-(5,6,7,8-tetrahydro-1-methoxy-2-naphthalenyl)-1-piperidinyl]butyl, $R^4$ is hydrogen, and L and M are CH, then $R^{12}$ is not cyano or chloro.

In some embodiments of formula (II) or (III), one or more of the following applies:

Y is —CH—;

L and M are both $CR^{13}$;

$R^{12}$ and $R^{13}$ are independently selected from hydrogen cyano, nitro, halo, —$C_{1-6}$alkyl, —$C_{2-6}$alkenyl, —$C_{2-6}$alkynyl, —C(=O)—$R^{14}$, —C(=O)—O—$R^{14}$, —O—C(=O)—$R^{14}$, —N($R^{14}$)$_2$, and —C(=O)—N(R)$_2$; especially —C(=O)—$R^{14}$, —C(=O)—O—$R^{14}$, —O—C(=O)—$R^{14}$, —N($R^{14}$)$_2$, and —C(=O)—N($R^{14}$)$_2$; more especially hydrogen;

each $R^{14}$ is independently selected from H or —$C_{1-6}$alkyl;

$R^{12}$ is hydrogen and L and M are both CH;

$R^2$ is selected from —C(=O)—$NR^3R^4$, —C(=S)—$NR^3R^4$, —CH=$CR^5R^6$, —$CH_2$—$OR^7$, —C(=O)—$OR^7$, —$CH_2$—$NR^3R^4$, —C(=O)—NH—$NR^3R^4$, —C(=O)—NH—$OR^7$, —NH—C(=O)—$NR^3R^4$, —O—C(=O)—$NR^3R^4$ and —CH($CF_3$)—$NR^3R^4$, especially —C(=O)—$NR^3R^4$, —$CH_2$—$OR^7$, —$CH_2$—$NR^3R^4$, —NH—C(=O)—$NR^3R^4$, —CH=$CR^5R^6$ and —CH($CF_3$)—$NR^3R^4$, more especially —C(=O)—$NR^3R^4$ or —CH($CF_3$)—$NR^3R^4$, most especially —C(=O)—$NR^3R^4$;

$R^3$ is selected from —$CHR^8R^{11}$ or —$C_{2-6}$alkyl-$R^{10}$; most especially —$CHR^8R^{11}$;

$R^4$ is hydrogen, alkyl, haloalkyl or perfluoroalkyl; especially hydrogen;

$R^3$ and $R^4$ taken together form a heterocyclyl or heteroaryl ring; especially where $R^3$ and $R^4$ form a monocyclic heterocyclyl or heteroaryl ring which is substituted by a cycloalkyl, cycloalkenyl, aryl, heterocyclyl or heteroaryl group, or where $R^3$ and $R^4$ form a bicyclic heterocyclyl or heteroaryl ring, or where $R^3$ and $R^4$ form a tricyclic spirane heterocyclyl group; more especially where $R^3$ and $R^4$ together form 1,2,3,4-tetrahydroisoquinolinyl,

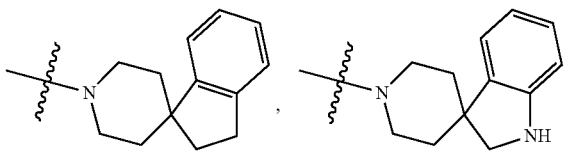 [SMILES: *N1CCC2(CCc3ccccc32)CC1 ; *N1CCC2(CC1)CNc1ccccc12]

which is optionally substituted at the ring nitrogen with a SO$_2$Me group, or piperidinyl which is substituted with benzimidazol-2-one or 1,3-benzoxazin-2-one;

R$^5$ is selected from —CHR$^8$R$^9$, —CHR$^8$R$^{11}$ or —C$_{0-6}$alkyl-R$^{10}$; especially CHR$^8$R$^9$, —CHR$^8$R$^{11}$ or —C$_{1-6}$alkyl-R$^{10}$; more especially —CHR$^8$R$^{11}$ or —C$_{2-6}$alkyl-R$^{10}$; most especially —CHR$^8$R$^{11}$;

R$^6$ is hydrogen, alkyl or haloalkyl; especially hydrogen;

R$^5$ and R$^6$ taken together form a heterocyclyl or heteroaryl ring;

R$^7$ is selected from —CHR$^8$R$^9$, —CHR$^8$R$^{11}$ and —C$_{0-6}$alkyl-R$^{10}$; especially —CHR$^8$R$^9$, —CHR$^8$R$^{11}$ and —C$_{1-6}$alkyl-R$^{10}$; more especially —CHR$^8$R$^{11}$ and —C$_{2-6}$alkyl-R$^{10}$; most especially —CHR$^8$R$^{11}$;

R$^8$ is selected from —CO$_2$H, —CONH$_2$, cycloalkyl, cycloalkenyl, aryl, heterocyclyl, heteroaryl, —C$_{1-6}$alkylR$^{10}$, —C$_{2-6}$alkenylR$^{10}$ and —C$_{2-6}$alkynylR$^{10}$; especially —CONH$_2$, aryl, heterocyclyl, heteroaryl, —C$_{1-6}$alkylR$^{10}$, —C$_{2-6}$alkenylR$^{10}$ and —C$_{2-6}$alkynylR$^{10}$; more especially —CONH$_2$, aryl and —C$_{1-6}$alkylR$^{10}$; more especially —CONH$_2$ and aryl; most especially napthyl, —CONH$_2$ and phenyl, R$^9$ is selected from —C$_{1-6}$alkyl, —C$_{1-6}$perfluoroalkyl, —C$_{2-6}$alkenyl, —C$_{2-6}$alkynyl, —C$_{0-6}$alkylOH, —C$_{0-6}$alkylCO$_2$H, —C$_{0-6}$alkylCONH$_2$, —C$_{0-6}$alkylNH$_2$, —C$_{0-6}$alkylSH, —C$_{0-6}$alkylSC$_{1-6}$alkyl, —C$_{0-6}$alkylNHC(=NH)NH$_2$, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$perfluoroalkyl, —C$_{0-6}$alkylOH, —C$_{0-6}$alkylNH$_2$, —C$_{0-6}$alkylSH, —C$_{0-6}$alkylSC$_{1-6}$alkyl, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$ perfluoroalkyl or —C$_{0-6}$alkylaryl; more especially C$_1$alkylaryl, aryl, methyl or —CF$_3$; most especially —CH$_2$-phenyl, phenyl, methyl or —CF$_3$;

R$^{11}$ is selected from —C$_{1-6}$alkyl, —C$_{1-6}$ perfluoroalkyl, —C$_{0-6}$alkylOH, —C$_{0-6}$alkylNH$_2$, —C$_{0-6}$alkylSH, —C$_{0-6}$alkylSC$_{1-6}$alkyl, —C$_{0-6}$alkylcycloalkyl, —C$_{0-6}$alkylaryl, —C$_{0-6}$alkylheterocyclyl and —C$_{0-6}$alkylheteroaryl; more especially —C$_{1-6}$alkyl, —C$_{1-6}$perfluoroalkyl or —C$_{0-6}$alkylaryl; more especially C$_1$alkylaryl, aryl, methyl or —CF$_3$; most especially —CH$_2$-phenyl, phenyl, methyl or —CF$_3$;

R$^{16}$ is selected from hydrogen, alkyl, haloalkyl or perfluoroalkyl; especially hydrogen;

R$^{17}$ is selected from hydrogen, —C$_{1-6}$alkyl, —C$_{1-6}$haloalkyl, —C$_{0-6}$alkylOH, —C$_{0-6}$alkylSH, —C$_{0-6}$alkylSC$_{1-6}$alkyl, —C$_{0-6}$alkylcycloalkyl; more especially hydrogen, —C$_{1-6}$alkyl, —C$_{1-6}$perfluoroalkyl, —C$_{0-6}$alkylcycloalkyl; most especially methyl or —CF$_3$;

wherein each alkyl, alkenyl, alkynyl, cycloalkyl, cycloalkenyl, aryl, heterocyclyl and heteroaryl are optionally substituted with one or more optional substituents.

As used herein, the term "alkyl" refers to a straight chain or branched saturated hydrocarbon group having 1 to 12 carbon atoms. Where appropriate, the alkyl group may have a specified number of carbon atoms, for example, —C$_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl, decyl, undecyl and dodecyl.

As used herein, the term "alkenyl" refers to a straight-chain or branched hydrocarbon group having one or more double bonds between carbon atoms and having 2 to 12 carbon atoms. Where appropriate, the alkenyl group may have a specified number of carbon atoms. For example, —C$_2$-C$_6$ as in "C$_2$-C$_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, undecenyl and dodecenyl.

As used herein, the term "alkynyl" refers to a straight-chain or branched hydrocarbon group having one or more triple bonds between carbon atoms and having 2 to 12 carbon atoms. Where appropriate, the alkynyl group may have a specified number of carbon atoms. For example, —C$_2$-C$_6$ as in "C$_2$-C$_6$alkynyl" includes groups having 2, 3, 4, 5 or 6 carbon atoms in a linear or branched arrangement. Examples of suitable alkynyl groups include, but are not limited to, ethynyl, propynyl, butynyl, pentynyl, hexynyl, octynyl, nonynyl, decynyl, undecynyl and dodecynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. The cycloalkyl group may also comprise two or three rings in which at least one ring is a cycloalkyl group. When there are two or three rings, each ring is linked to one or more of the other rings by sharing one or more ring atoms forming a spirane or fused ring system. The cycloalkyl group also include a carbonyl group attached to a ring carbon atom. Examples of suitable cycloalkyl groups include, but are not limited to, cyclopropyl, cyclobutyl, cyclopentanyl, cyclohexanyl, cycloheptanyl, cyclooctanyl, decahydronaphthalyl, bicyclo[3.1.0]hexanyl, bicyclo[4.1.0]heptanyl, bicyclo[3.1.1]heptanyl, bicyclo[2.2.1]heptanyl, adamantanyl and spiranes such as spiro[4.5]decane.

As used herein, the term "cycloalkenyl" refers to a cyclic hydrocarbon having at least one double bond, which is not aromatic. The cycloalkenyl ring may include a specified number of carbon atoms. For example, a 4 to 8 membered cycloalkenyl group contains at least one double bond and 4, 5, 6, 7 or 8 carbon atoms. The cycloalkenyl group may also comprise two or three rings, provided that at least one ring is a cycloalkenyl ring. When there are two or three rings, each ring is linked to one or more of the other rings by sharing one or more ring atoms forming a spirane or fused ring system. The cycloalkenyl group may also include a carbonyl group attached to an unsaturated ring carbon atom. Examples of suitable cycloalkenyl groups include, but are not limited to cyclopentenyl, cyclopenta-1,3-dienyl, cyclohexenyl, cyclohexen-1,3-dienyl and cyclohexen-1,4-dienyl.

As used herein, the term "aryl" is intended to mean any stable, monocyclic, bicyclic or tricyclic carbon ring of up to 7 atoms in each ring, wherein at least one ring is aromatic. When more than one ring is present, the rings may be fused to one another. Examples of aryl groups include, but are not limited to, phenyl, naphthyl, tetrahydronaphthyl, indanyl, biphenyl, binaphthyl, anthracenyl, phenanthrenyl, phenalenyl and fluorenyl.

The term "heterocyclic" or "heterocyclyl" as used herein, refers to a cycloalkyl or cycloalkenyl group in which one or more carbon atoms have been replaced by heteroatoms independently selected from N, S and O. For example, between 1 and 4 carbon atoms in each ring may be replaced by heteroatoms independently selected from N, S and O. The heterocyclic group may be monocyclic, bicyclic or tricyclic in which at least one ring is heterocyclic. When there are two or three rings, each ring is linked to one or more of the other rings by sharing one or more ring atoms forming a spirane or fused ring system. The heterocyclyl group may also include a carbonyl group attached to an unsaturated ring carbon. Examples of suitable heterocyclyl groups include tetrahydrofuranyl, tetrahydrothiophenyl, pyrrolidinyl, 2-pyrrolidonyl, pyrrolinyl, dithiolyl, 1,3-dioxolanyl, pyrazolinyl, imidazolinyl, imidazolidinyl, 1,4-dioxanyl, 1,3-dioxanyl, dioxinyl, piperidinyl, piperazinyl, morpholinyl, thiomorpholinyl, pyranyl, 1,4-dithiane, 1,3,5-trithiane, quinuclidine and tetrahydropyranyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. When more than one ring is present the rings may be fused. The heteroaryl group may also include a carbonyl group attached to an unsaturated carbon in the ring system. Examples of suitable heteroaryl groups include pyrrolyl, furanyl, thienyl, pyrazolyl, imidazolyl, 1,2,4-triazolyl, 1,2,3-triazolyl, isoxazolyl, oxazolyl, thiazolyl, isothiazolyl, oxadiazolyl, oxatriazolyl, pyridinyl, pyridazinyl, pyrimidinyl, pyrazinyl, triazinyl, azepinyl, oxepinyl, thiepinyl, diazepinyl, coumaranyl, benzofuranyl, isobenzofuranyl, benzothienyl, indolyl, indolinyl, isoindolyl, benzimidazolyl, benzisoxazolyl, benzoxazolyl, benzisoxazolyl, benzothiazolyl, 1-benzopyranyl, 2-benzopyranyl, benzopyran-2-on-yl, benzopyran-1-on-yl, quinolinyl, tetrahydroquinolinyl, isoquinolinyl, quinazolinyl, cinnolinyl, quinoxalinyl, tetrahydroquinoxalinyl, naphthyridinyl, acridinyl, carbazolyl, xanthenyl, phenazinyl, phenothiazinyl, phenoxazinyl, 1,4-benzodiazepin-2-on-yl, 1,5-benzodiazepin-2-on-yl, 1,4-benzodiazepin-2,5-dion-yl, pyrrolo[2,1-c][1,4]benzodiazepine-5,11-dion-yl, 1,4-benzothiazepin-5-on-yl, 5,11-dihydro-benzo[e]pyrido[3,2-b][1,4]-diazepin-6-on-yl, chromonyl, pyranocoumarinyl, 3,4-dihydroquinoxalin-2-on-yl, quinazolinonyl, quinazolindionyl, imidazoquinoxalinyl, 2,3-dihydrospiro[indene-1,4'-piperidine] and spiro[indoline-3,4'-piperidine].

The cycloalkyl, cycloalkenyl, aryl, heterocyclyl or heteroaryl group may advantageously be a privileged substructure or form part of a privileged substructure. Privileged substructures are molecular frameworks able to provide ligands for diverse receptors. Examples of privileged substructures include biphenyl, arylpiperidine, arylpiperazine, aryl-1,4-dihydropyridine, aryl-dihydropyrimidone, 1,4-benzodiazepin-2-one, 1,5-benzodiazepin-2-one, 1,4-benzodiazepin-2,5-dione, pyrrolo[2,1-c][1,4]benzodiazepine-5,11-dione, 1,4-benzothiazepin-5-one, 5,11-dihydro-benzo[e]pyrido[3,2-b][1,4]-diazepin-6-one, benzopyran, chromone, coumarin, pyranocoumarin, 3,4-dihydroquinoxalin-2-one, quinazolinone, quinazolindione, imidazoquinoxaline, indole, benzimidazole, benzofuran and benzothiophene. Other privileged substructures would be known to a person skilled in the art. The privileged substructure may be optionally substituted.

Unless otherwise defined, the term "optionally substituted" means, for example, that each alkyl, alkenyl, alkynyl, cycloalkyl, cycloalkenyl, aryl, heterocyclyl and heteroaryl (including thienyl and thiazolyl), whether an individual entity or as part of a larger entity, may be optionally substituted with one or more optional substituents selected from $R^{15}$, $R^{15}$—O—$(CH_2)_q$—, $R^{15}$—S—$(CH_2)_q$—, hydroxyl$(CH_2)_q$—, HS—$(CH_2)_q$—, $R^{15}$—C(=O)—O—$(CH_2)_q$—, $R^{15}$—O—C(=O)—$(CH_2)_q$—, $R^{15}$—C(=O)—$(CH_2)_q$—, $(R^{15})_2$N—C(=O)—$(CH_2)_q$—, $R^{15}S(O)_j$—$(CH_2)_q$—, $(R^{15})_2$N—$(CH_2)_q$—, cyano, nitro and halo, wherein each $R^{15}$ is independently selected from H, alkyl, alkenyl, alkynyl, —$(CH_2)_i$-aryl, —$(CH_2)_i$-heteroaryl, —$(CH_2)_i$-cycloalkyl, —$(CH_2)_i$-cycloalkenyl or —$(CH_2)_i$-heterocyclyl; q and i are 0 or an integer from 1 to 6, and j is 0 or an integer of 1 or 2. Furthermore, the alkyl, alkenyl, alkynyl, aryl, heteroaryl, cycloalkyl, cycloalkenyl and heterocyclyl groups within the optional substituents may be further optionally substituted with one or more substituents selected from cyano, hydroxyl, nitro, halo, alkyl, haloalkyl, alkenyl, alkynyl or alkoxyl groups.

In one embodiment, the optional substituents include fluoro, chloro, methyl, ethyl, propyl, isopropyl, butyl, tert-butyl, hydroxy, methoxy, ethoxy, propoxy, isopropoxy, hydroxymethyl, trifluoromethyl, trifluoromethoxy, cyano, nitro, acetyl, amino, methylamino, dimethylamino, —CO—$NH_2$, —$CO_2H$, —$COCH_3$, —$SO_2CH_3$, benzimidazol-2-one, 1,3-benzoxazin-2-one, tetrazole, piperidinyl, piperazinyl, 1,4-dihydropyridinyl, dihydropyrimidonyl, phenyl and benzyl in which the phenyl or benzyl ring is optionally substituted with halo, methyl, methoxy, phenyl, tetrazole, piperidinyl, piperazinyl, 1,4-dihydropyridinyl or dihydropyrimidonyl; especially hydroxy, amino, hydroxymethyl, phenyl, cyano, —CO—$NH_2$, —$CO_2H$, —$COCH_3$, benzimidazol-2-one and 1,3-benzoxazin-2-one.

As used herein, the term "halogen" or "halo" refers to fluorine (fluoro), chlorine (chloro), bromine (bromo) and iodine (iodo).

As used herein, the term "haloalkyl" refers to an alkyl group (as defined above) in which one or more hydrogen atoms are replaced with halogen atoms. "Haloalkyl" includes perhaloalkyl groups in which all hydrogen atoms are replaced with halogen atoms. Examples of haloalkyl groups include fluoromethyl, difluoromethyl, trifluoromethyl, chloromethyl, dichloromethyl, trichloromethyl, bromomethyl, dibromomethyl, iodomethyl, diiodomethyl, 1-fluoroethyl, 2-fluoroethyl, 1,2-difluoroethyl, 1-chloroethyl, 2-chloroethyl, 1,2-dichloroethyl. Perhaloalkyl groups include perfluoroalkyl groups such as trifluoromethyl and pentafluoroethyl and perchloroalkyl groups such as trichloromethyl and pentachloromethyl.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds and salts of the invention may be presented in the form of a prodrug. The term "prodrug" is used in its broadest sense and encompasses those derivatives that are converted in vivo to the compounds of the invention. A prodrug may include modifications to one or more of the functional groups of a compound of the invention.

The phrase "a derivative which is capable of being converted in vivo" as used in relation to another functional group includes all those functional groups or derivatives which upon administration into a mammal may be converted into the stated functional group. Those skilled in the art may readily determine whether a group may be capable of being converted in vivo to another functional group using routine enzymatic or animal studies.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

Compounds of formula (I), (II) and (III) possess a heteroaryl moiety linked to a thienyl or thiazolyl moiety through a single bond. A person skilled in the art would be aware of reactions to link two heteroaryl moieties, for example using the Suzuki reaction. In the Suzuki reaction a heteroaryl halide, such as a bromide, or heteroaryl triflate is mixed with a heteroaryl borane in the presence of a palladium catalyst and base to produce a biheteroaryl moiety. Suitable palladium catalysts would be known to a person skilled in the art and include tetrakis-(triphenylphosphine)palladium(0). A range of bases also may be used, such as caesium fluoride and sodium carbonate.

One or both of the heteroaryl rings employed in the Suzuki reaction may be further functionalised before, or after the reaction. In one example, if an ester-substituted heteroaryl bromide is used in the above reaction, then following the reaction the ester group may be hydrolysed, and then treated with various other reagents to form, for example, an amide bond, a reduced amide, an alkenyl bond, an ester, or an ether. This step may be used to incorporate functionality at, for example, $R^2$ or to the thienyl moiety or thiazolyl moiety (for compounds of formula (I)), or $R^2$, $R^{12}$ or $R^{13}$ (for compounds of formula (II) or (III)).

Other methods to prepare compounds of formula (I), (II) and (III) would be known to a person skilled in the art. Two general procedures are outlined below in the Examples.

A person skilled in the art will be aware that during synthesis, of the compounds of the invention, some substituents may be reactive under conditions used and must be disguised or protected to prevent unwanted side reactions. Suitable protecting groups for protecting reactive groups from unwanted reactions are provided in Green and Wuts, Protective Groups in Organic Synthesis.

While it is possible that, for use in therapy, a compound of the invention may be administered as a neat chemical, the active ingredient is especially presented as a pharmaceutical composition.

Thus, in a further aspect of the invention there is provided a pharmaceutical composition comprising a compound of formula (II) or (III) and at least one pharmaceutically acceptable carrier.

The carrier(s) must be "acceptable" in the sense of being compatible with the other ingredients of the composition and not deleterious to the recipient thereof.

Pharmaceutical compositions include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity, in suitable proportions and compacted in the shape and size desired.

The powders and tablets especially contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient, sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising, spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal formulations, the compound will generally have a small particle size for example of the order of 1 to 10 microns or less. Such a particle size may be obtained by means known in the art, for example by micronization.

When desired, compositions adapted to give sustained release of the active ingredient may be employed.

The pharmaceutical preparations are especially in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In one embodiment, the composition is a liquid or powder for intranasal administration, a tablet or capsule for oral administration or a liquid for intravenous administration.

The invention will now be described with reference to the following Examples which illustrate some aspects of the present invention. However, it is to be understood that the particularity of the following description of the invention is not to supersede the generality of the preceding description of the invention.

EXAMPLES

Synthesis

Nuclear Magnetic Resonance spectra were recorded at 400 MHz ($^1$H)/100 MHz ($^{13}$C) on a Varian Gemini-400. $^1$H and $^{13}$C chemical shifts (δ) are given in parts per million (ppm) using residual protonated solvent (DMSO-$d_6$) as an internal standard. Coupling constants are given in Hertz (Hz). The following abbreviations are used: s=singlet, d=doublet, t=triplet, m=multiplet, bs=broad signal. Low resolution mass spectral data were recorded on a API2000 (TOF MS ES+) instrument (Applied Biosystems). High resolution mass spectral data was obtained on a PE Sciex API QSTAR Pulsar (ES-qTOF) (Perkin Elmer, Waltham, Mass., USA) instrument using ACP (acyl carrier protein) (65-714) ($C_{47}H_{75}N_{12}O_{16}$ (M+H), 1063.5424) and reserpine ($C_{33}H_{40}N_2O_9$ (M+H), 609.2812) as internal references. Resolution for the instrument was set between 10,000 and 12,000 for all standards. Analytical reversed-phase high performance liquid chromoatography (HPLC) was performed on a Gemini $C_{18}$ column (4.6×250 mm) (Phenomenex, Lane Cove, NSW, Australia). Preparative reversed phase HPLC was performed on a Gemini 10µ $C_{18}$ column (22×250 mm) (Phenomenex) or Jupiter 10µ 300 Å $C_{18}$ column (21.2×250 mm) (Phenomenex). Separations were achieved using linear gradients of buffer B in A (A=0.1% aqueous TFA; B=90% $CH_3CN$, 10% $H_2O$, 0.09% TFA) at a flow rate of 1 mL/min (analytical) and 20 mL/min (preparative).

Rink amide resin (sv=0.65 mM/g), 2-(1H-Benzotriazol-1-yl)-1,1,3,3-tetramethyluronium hexafluorophosphate (HBTU) and all $N_\alpha$-Fmoc-amino acids were peptide synthesis grade purchased from IRIS Biotech (Marktredwitz, Germany). Dichloromethane, diisopropylethylamine, N,N-dimethylformamide, and trifluoroacetic acid were obtained from Auspep (Parkville, VIC, Australia). HPLC grade acetonitrile and methanol were purchased from Labscan (Gliwice, Poland). All other reagents and solvents were purchased from Sigma-Aldrich, Alfa Aesar (Lancashire, England), Combi-Blocks (San Diego, Calif., USA), Oakwood Products (West, Columbia, S.C., USA), Frontier Scientific (Logan, Utah, USA), Boron Molecular (Noble Park, VIC, Australia) and Trans World Chemicals (Rockville, Md., USA). Abbreviations: TFA, trifluoroacetic acid; DCM, dichloromethane; EtOAc, ethyl acetate; EtOH, ethanol; DMSO, dimethylsulfoxide; DMF, N,N-dimethylformamide; HBTU, O-benzotriazol-1-yl-N,N,N',N'-tetramethyluronium hexafluorophosphate; PyBrOP, benzotriazole-1-yloxytripyrrolidinophosphonium hexafluorophosphate; DIEA, N,N-diisopropylethylamine; Pd(PPh$_3$)$_4$, Tetrakis-(triphenylphosphine)palladium(0); CsF, caesium fluoride; CuI, copper(I)iodide; MgSO$_4$, magnesium sulphate.

General, Procedure a (On-Resin Synthesis)

Functionalized Rink amide polystyrene resin (0.325 mM, 0.5 g) was derivatized with Fmoc-AA using in situ neutralization/HBTU activation protocols for Fmoc chemistry. After removal of the Fmoc group to provide a primary amine, a carboxy-substituted heteroaryl bromide was coupled to the primary amine.

The bromoheteroaryl-functionalized resin (0.325 mM) was placed in a reaction vessel under nitrogen atmosphere. Dimethylether (DME) (5 mL) was degassed and added to the resin, followed by addition of neat Pd(PPh$_3$)$_4$ (81 mg, 0.07 mM). A solution of a thiopheneboronic acid or thiazoleboronic acid (1.3 mM) in degassed EtOH (1 mL) was added to the resin, and the mixture was agitated for 5 min; CsF (162 mg, 1.3 mM) was added neat. The mixture was agitated 16 h at 60° C. before excess reagents were removed by filtration, and the resin was washed with DMF (3×) and DCM (3×) to yield resin bound compound.

The resin was dried for several hours under reduced pressure and placed in a cleavage vessel. The resin was treated with a mixture of TFA/H$_2$O 92:8 for an hour. TFA was blown off under nitrogen atmosphere and the dry cleaved crude product was re-dissolved in a solution of 30% A and 70% B (as defined above) and separated from the resin. Preparative HPLC, followed by freeze-drying, gave the pure product as a white solid material.

General Procedure B (Solution Based Synthesis)

An ester-substituted heteroaryl bromide (1.5 mM) was dissolved in toluene (7 mL) and in a separate vessel a thiopheneboronic acid or thiazoleboronic acid (2.0 mM) was dissolved in toluene (7 mL) and ethanol (1.5 mL). 2.0 mL of sodium carbonate (2.5 M) was added to the dissolved ester-substituted heteroaryl bromide. The catalyst Pd(PPh$_3$)$_4$ (35 mg, 0.03 mM) was added to the dissolved ester-substituted heteroaryl bromide followed by the dissolved thiophene- or thiazole-boronic acid, and the flask was evacuated and refilled with argon five times. The mixture was stirred at 80° C. for 2 hours. The mixture was filtered through celite with EtOAc (100 mL). The organic layer was separated, dried over MgSO$_4$ and the solvent was removed under reduced pressure. Preparative HPLC, followed by freeze-drying, gave the pure product as a white solid material.

The pure fractions were collected and the ester group was hydrolysed with 1 M lithium hydroxide (LiOH) in tetrahydrofuran (THF) for 16 h. The solvent was removed under reduced pressure receiving the compound with a free acid.

The functionalized carboxylic acid (1 eq) and amine (2 eq) were placed in a reaction vessel under nitrogen atmosphere. PyBrOP (2 eq) was added neat together with DIEA (2.2 eq) and DMF. The mixture was stirred for 24 h at room temperature. Solvent was removed by evaporation using a GeneVac Atlas HT-8 speed evaporation system. Preparative HPLC, followed by freeze-drying of the appropriate fractions, gave the pure product as a white solid material.

Example Compounds

N-(1-amino-1-oxo-3-phenylpropan-2-yl)-6-(thiophen-2-yl)-nicotinamide (3) was prepared via procedure A, using Fmoc-protected-L-phenylalanine (1.3 mM), 6-bromopyridine-3-carboxylic acid (0.975 mM) and 2-thiopheneboronic acid (1.3 mM). Yield (7.5 mg, 6.57%); $^1$H NMR (400 MHz, DMSO-d$_6$): δ 2.94 (dd, J=10.8 Hz, J=30 Hz, 1H), 3.12 (dd, J=9.2 Hz, J=30 Hz, 1H), 4.64 (ddd, J=8.4 Hz, J=9.2 Hz, J=10.8 Hz, 1H), 7.12 (bs, 1H), 7.13-7.34 (m, 6H), 7.58 (bs, 1H), 7.69 (dd, J=1.2 Hz, J=4.8 Hz, 1H), 7.87 (dd, J=1.2 Hz, J=3.6 Hz, 1H), 7.97 (d, J=8.1 Hz, 1H), 8.13 (dd, J=2 Hz, J=8.4 Hz, 1H), 8.71 (d, J=8.4 Hz, 1H), 8.83 (d, J=0.8 1H). $^{13}$C NMR (100 MHz, DMSO-d$_6$): δ 173.6, 164.9, 154.2, 149.1, 144.0, 138.9, 136.6, 130.2, 129.6 (2C), 129.1, 128.5 (2C), 128.1, 127.1, 126.7, 118.4, 55.1, 37.7. ESI-HRMS calculated for $C_{19}H_{17}N_3O_2S$ [M+H]$^+$352.1119. Found: 352.1109.

N-benzhydryl-6-(thiophen-2-yl)nicotinamide (4) was prepared via procedure B, using methyl 6-bromopicolinate (1.5 mM), 2-thiopheneboronic acid (2 mM) and benzhydrylamine (2 eq). Yield (0.45 mg/0.7%); ESI calculated for $C_{23}H_{18}N_2OS$ [M+H]$^+$: 370.1. Found: 371.0.

N-benzyl-6-(thiophen-2-yl)nicotinamide (5) was prepared via procedure B, using methyl 6-bromopicolinate (1.5 mM), 2-thiopheneboronic acid (2 mM) and phenylmethanamine (2 eq). Yield (5.38 mg/9.1%); $^1$H NMR (400 MHz, DMSO-d$_6$): δ 4.50 (d, J=6 Hz, 2H), 7.19 (t, J=9.6 Hz, 1H), 7.22 (q, J=17.6 Hz, 1H), 7.27-7.33 (m, 4H), 7.70 (d, J=4.8 Hz, 1H), 7.89 (d, J=3.6 Hz, 1H), 8.01 (d, J=8.4 Hz, 1H), 8.25 (dd, J=1.6 Hz, J=8.4 Hz, 1H), 8.97 (d, J=2.4 Hz, 1H), 9.19 (t, J=11.6 Hz 1H). ESI calculated for $C_{17}H_{14}N_2OS$ [M+H]$^+$: 294.1. Found: 295.1.

(3,4-dihydroisoquolin-2(1H)-yl)(6-(thiophen-2-yl)pyridin-3-yl)methanone (6) was prepared via procedure B, using methyl 6-bromopicolinate (1.5 mM), 2-thiopheneboronic acid (2 mM) and 1,2,3,4-tetrahydroisoquinoline (2 eq). Yield (12.67 mg/22%); $^1$H NMR (400 MHz, DMSO-d$_6$): δ 2.81 (d, J=11.6 Hz, 2H), 3.61 (s, 1H), 3.84 (s, 1H), 4.64 (s, 1H), 4.76 (s, 1H), 7.06-7.25 (m, 6H), 7.69 (d, J=4.8 Hz, 1H), 7.88 (d, J=4 Hz, 1H), 7.91 (d, J=8.4 Hz, 1H), 8.00 (d, J=8.4 Hz, 1H), 8.61 (d, J=0.8 Hz, 1H). $^{13}$C NMR (100 MHz, DMSO-d$_6$): δ 169.3, 153.1, 148.1, 144.2, 136.5, 134.8, 133.3, 130.5, 129.8, 129.1 (2C), 127.0, 126.8, 126.7, 118.7, 113.7, 49.5, 44.8, 29.3. ESI calculated for C$_{19}$H$_{16}$N$_2$OS [M+H]$^+$: 320.1. Found: 321.0.

(2,3-dihydrospiro[indene-1,4'-piperidin]-1'-yl)(6-(thiophen-2-yl)pyridin-3-yl)methanone (7) was prepared via procedure B, using methyl 6-bromopicolinate (1.5 mM), 2-thiopheneboronic acid (2 mM) and 2,3-dihydrospiro[indene-1,4'-piperidine] (2 eq). Yield (0.85 mg/2.1%). ESI calculated for C$_{23}$H$_{22}$N$_2$OS [M+H]$^+$: 374.2. Found: 375.0.

1-(4-phenyl-1-(6-(thiophen-2-yl)nicotinoyl)piperidin-4-yl)ethanone (8) was prepared via procedure B, using methyl 6-bromopicolinate (1.5 mM), 2-thiopheneboronic acid (2 mM) and 1-(4-phenylpiperidin-4-yl)ethanone (2 eq). Yield (2.48 mg/5.1%). ESI calculated for C$_{23}$H$_{22}$N$_2$O$_2$S [M+H]$^+$: 390.5. Found: 390.9.

4-((6-(thiophen-2-yl)nicotinamido)methyl)benzoic acid (9) was prepared via procedure B, using methyl 6-bromopicolinate (1.5 mM), 2-thiopheneboronic acid (2 mM) and 4-(aminomethyl)-benzoic acid (2 eq). Yield (2.78 mg/5.2%); $^1$H NMR (400 MHz, DMSO-d$_6$): δ 4.56 (d, J=6 Hz, 2H), 7.19 (t, J=8.8 Hz, 1H), 7.43 (d, J=8 Hz, 2H), 7.70 (d, J=5.2 Hz, 1H), 7.89-7.91 (m, 3H), 8.02 (d, J=8.4 Hz, 1H), 8.25 (dd, J=2.4 Hz, J=8.4 Hz, 1H), 8.98 (d, J=2.4 Hz, 1H), 9.26 (d, J=6 Hz, 1H). $^{13}$C NMR (100 MHz, DMSO-d$_6$): δ 167.6, 165.1, 154.4, 149.0, 144.9, 144.0, 136.5, 130.2, 129.9 (2C), 129.8, 129.2, 128.1, 127.7 (2C), 127.2, 118.6, 42.9. ESI calculated for C$_{18}$H$_{14}$N$_2$O$_3$S [M+H]$^+$: 338.1. Found: 339.0.

(1-(methylsulfonyl)spiro[indoline-3,4'-piperidin]-1'-yl)(6-(thiophen-2-yl)pyridin-3-yl)methanone (10) was prepared via procedure B, using methyl 6-bromopicolinate (1.5 mM), 2-thiopheneboronic acid (2 mM) and 1-(methylsulfonyl)spiro[indoline-3,4'-piperidine] (2 eq). Yield (16.26 mg/26.4%); $^1$H NMR (400 MHz, DMSO-d$_6$): δ 1.65 (s, 1H), 1.77 (s, 1H), 1.87 (d, J=10.8 Hz, 2H), 2.48 (d, J=1.6 Hz, 2H), 3.01-3.04 (m, 3H), 3.61 (s, 1H), 3.91-3.94 (m, 2H), 4.49 (s, 1H), 7.06 (t, J=13.2 Hz, 1H), 7.17-7.27 (m, 3H), 7.41 (d, J=7.6 Hz, 1H), 7.68 (dd, J=1.2 Hz, J=5.2 Hz, 2H), 7.87 (dd, J=1.2 Hz, J=3.8 Hz, 1H), 7.91 (dd, J=2.4 Hz, J=8.4 Hz, 1H), 7.98 (d, J=8.4 Hz, 1H), 8.61 (d, J=2.4 Hz, 1H). $^{13}$C NMR (100 MHz, DMSO-d$_6$): δ 167.2, 152.9, 148.0, 144.1, 141.4, 138.9, 136.5, 130.4, 129.7, 129.1, 128.9, 126.7, 124.3, 124.0, 118.7, 113.2, 58.7, 44.9, 43.2, 36.3, 35.8, 34.7 (2C). ESI calculated for C$_{23}$H$_{23}$N$_3$O$_3$S$_2$ [M+H]$^+$: 453.1. Found: 453.8.

1-(1-(6-(thiophen-2-yl)nicotinoyl)piperidin-4-yl)-1H-benzo[d]imidazol-2(3H)-one (11) was prepared via procedure B, using methyl 6-bromopicolinate (1.5 mM), 2-thiopheneboronic acid (2 mM) and 1-(piperidin-4-yl)-1H-benzo[d]imidazol-2(3H)-one (2 eq). Yield (14.04 mg/47.6%); $^1$H NMR (400 MHz, DMSO-d$_6$): δ 1.74 (s, 1H), 2.35 (m, 1H), 2.48 (s, 1H), 2.98 (s, 1H), 3.25 (s, 1H), 3.74 (s, 1H), 4.42 (m, 1H), 4.62 (s, 1H), 6.96 (d, J=6.8 Hz, 2H), 7.18 (t, J=12 Hz, 1H), 7.36 (d, J=7.6 Hz, 1H), 7.68 (d, J=4 Hz, 1H), 7.86 (d, J=1.6 Hz, 1H), 7.93 (d, J=1.6 Hz, 1H), 7.99 (d, J=7.6 Hz, 1H), 8.62 (d, J=0.8 Hz, 1H). $^{13}$C NMR (100 MHz, DMSO-d$_6$): δ 167.3, 154.2, 153.0, 148.0, 144.1, 136.5, 130.4, 129.7, 129.5, 129.1, 128.7, 126.7, 121.2, 121.0, 118.7, 109.4, 50.2, 47.3, 41.7, 29.5, 28.9. ESI calculated for C$_{22}$H$_{20}$N$_4$O$_2$S [M+H]$^+$: 404.1. Found: 404.9.

(S)—N-(1-(naphthalen-2-yl)ethyl)-6-(thiophen-2-yl)nicotinamide (12) was prepared via procedure B, using methyl 6-bromopicolinate (1.5 mM), 2-thiopheneboronic acid (2 mM) and (S)-1-(naphthalen-2-yl)ethanamine (2 eq). Yield (12.3 mg/14.5%); $^1$H NMR (400 MHz, DMSO-d$_6$): δ 1.58 (d, J=7.2 Hz, 3H), 5.30-5.37 (m, 1H), 7.19 (t, J=5.2 Hz, 1H), 7.44-7.51 (m, 5H), 7.58 (dd, J=1.6 Hz, J=8.4 Hz, 1H), 7.70 (dd, J=0.8 Hz, J=5 Hz, 1H), 7.85-7.88 (m, 3H), 7.90 (d, J=3.2 Hz, 2H), 8.00 (d, J=8.4 Hz, 1H), 8.26 (dd, J=2 Hz, J=8.2 Hz, 1H), 8.98 (d, J=2.4 Hz, 1H), 9.06 (d, J=8 Hz, 1H). $^{13}$C NMR (100 MHz, DMSO-d$_6$): δ 164.3, 154.3, 149.2, 142.5, 136.6, 133.3, 132.1, 130.1, 129.1, 128.4 (2C), 128.1 (2C), 127.9, 127.1, 126.6, 126.1, 125.4, 124.6, 118.4, 49.2, 22.5. ESI calculated for C$_{22}$H$_{18}$N$_2$OS [M+H]$^+$: 358.1. Found: 358.9.

1-(1-(6-(thiophen-2-yl)nicotinoyl)piperidin-4-yl)-1H-benzo[d][1,3]oxazin-2(4H)-one (13) was prepared via procedure B, using methyl 6-bromopicolinate (1.5 mM), 2-thiopheneboronic acid (2 mM) and 1-(piperidin-4-yl)-1H-benzo[d][1,3]oxazin-2(4H)-one (2 eq). Yield (26.3 mg/43.2%); $^1$H NMR (400 MHz, DMSO-d$_6$): δ 1.83 (d, J=26.8 Hz, 2H), 2.46 (d, J=16 Hz, 2H), 2.96 (s, 1H), 3.33 (s, 1H), 3.72 (s, 1H), 4.20-4.22 (m, 1H), 4.61 (s, 1H), 5.12 (s, 2H), 7.10 (t, J=14.4 Hz, 1H), 7.17-7.18 (m, 1H), 7.27 (d, J=7.2 Hz, 1H), 7.32-7.39 (m, 2H), 7.67 (dd, J=1.2 Hz, J=5 Hz, 1H), 7.86 (dd, J=1.2 Hz, J=2.4 Hz, 1H), 7.87 (dd, J=1.2 Hz, J=2 Hz, 1H), 7.98 (d, J=8.4 Hz, 1H), 8.56 (d, J=2 Hz, 1H). $^{13}$C NMR (100 MHz, DMSO-d$_6$): δ 167.1, 153.0, 152.4, 148.0, 144.1, 138.9, 136.4, 130.4, 129.8, 129.5, 129.1, 126.7, 125.3, 123.5, 123.1, 118.7, 114.6, 66.8, 55.7, 47.2, 41.9, 29.1, 28.2. ESI calculated for C$_{22}$H$_{21}$N$_3$O$_3$S [M+H]$^+$: 419.1. Found: 419.9.

Further example compounds are shown in Table 1 below.

Biological Assays

Materials

Glutathione, 1-chloro-2,4-dinitrobenzene, indomethacin, nocodazole, were purchased from Sigma-Aldrich Pty Ltd (Castle Hill, NSW, Australia). Compounds 1 and 2 are known inhibitors of H-PGDS (Aritake, 2006; Hohwy, 2008). Compound 1 (HQL-79) was obtained from Cayman Chemical (Ann Arbor, Mich., USA). Compound 2 was purchased at Ryan Scientific (Mt. Pleasant, S.C., USA).

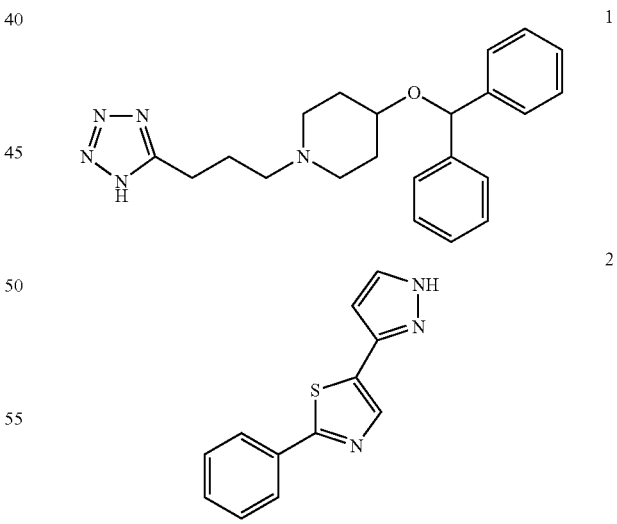

Protein Expression and Purification

H-PGDS was expressed and purified as described previously (Jowsey, 2001). Briefly, H-PGDS was expressed in *Escherichia coli* strain BL21 DE3 transformed with the pET17b HPGDS expression construct, grown overnight at 37° C. in 250 ml of Luria-Bertani medium supplemented with 100 μg/ml ampicillin. After 24 h, without induction, bacteria were harvested by centrifugation at 5000 g for 20 min at 4° C.; cell pellets were kept at −70° C. until required. Cells were resuspended in 25 ml of ice-cold phosphate buffered saline (PBS), pH 7.4, containing 1 mM DTT, 0.5% Triton X-100 and EDTA-free protease inhibitor tablets (F. Hoffmann-La Roche, Dee Why, NSW, Australia); and incubated with rotation for 30 mins at 4° C. Cells were then lysed by sonication at 90-100 W over 3×1 min intervals, while incubated on ice; the lysate clarified by centrifugation at 18000 g for 10 min at 4° C.

The supernatant was then applied to a GSTPrep FF 16/10 column pre-equilibrated with PBS, pH 7.4, and 1 mM DTT, at 0.4 ml/minute using an AKTA explorer 100 (GE Healthcare, Rydalmere, NSW, Australia), then washed with 5 column volumes of the same buffer at 1 ml/min. Bound H-PGDS was eluted in 5 column volumes of 15 mM reduced glutathione in 50 mM Tris, pH 9.0, at 0.5 ml/min, and dialysed against 100 volumes of 5 mM TrisCl, pH 8.0. The protein was concentrated to 20 mg/ml, as determined by the method of Bradford (Bradford, 1976) using an Amicon Ultra-4 centrifugal filter device (Millipore, North Ryde, NSW, Australia) following manufacturers recommendations. Glycerol was added to a final concentration of 10% (v/v) prior to storage at −20° C.

Enzyme Assays

The H-PGDS catalyzed conjugation of GSH and 1-chloro-2,4-dinitrobenzene (CDNB) was used as the biochemical assay for enzyme inhibition. Reactions were performed in 96 well plate format, and product formation was followed at A340 nm over a 10 min interval at 25° C. using a POWERWAVE XS microplate scanning spectrophotometer (Bio-Tek Instruments, Winooski, Vt., USA). Reactions were performed in 0.1 M Tris HCl, pH 8.0 containing 2 mM $MgCl_2$, 1 mM CDNB, 2 mM GSH, 2.5 ng/μl purified H-PGDS and 10% (v/v) ethanol in a 200 μl reaction volume. $IC_{50}$ values were calculated from rates of conjugation activity determined at eight concentration points bracketing the $IC_{50}$, where compound solubility allowed, and were corrected for background activity at the same solvent concentrations. All compounds were made up in 100% DMSO and diluted with 0.1 M Tris HCl, pH 8.0 with 2 mM $MgCl_2$. $I_{50}$ and $IC_{50}$ values were determined at a final DMSO composition of no greater than 4% v/v for all compounds. Non-linear regression analysis and $IC_{50}$ calculations were performed using GraphPad Prism version 4.0c. The results are shown in Table 1.

TABLE 1

| Compound | $R^2$ | $R^1$ | Mass/yield | $I_{[50]}$ | $IC_{50}$ (μM) |
|---|---|---|---|---|---|
| 3 | (S)-2-amino-3-phenylpropanamide-N-acetyl (phenylalaninamide acetamide) | 2-thienyl | 7.5 mg/6.6% | 97.0 ± 2.4 | 1.2 ± 1.0 |
| 4 | N-benzhydryl acetamide | 2-thienyl | 0.45 mg/0.7% | 28.5 | — |
| 5 | N-benzyl acetamide | 2-thienyl | 5.38 mg/9.1% | 99.5 ± 0.8 | 0.597 ± 1.2 |
| 6 | 1-(3,4-dihydroisoquinolin-2(1H)-yl)ethanone | 2-thienyl | 12.67 mg/22% | 72.3 ± 1.5 | n/a- |

TABLE 1-continued

| Compound | R² | R¹ | Mass/yield | I[50] | IC₅₀ (μM) |
|---|---|---|---|---|---|
| 7 | spiro[indane-piperidine] acyl | 2-thienyl | 0.85 mg/2.1% | 91.0 ± 0.1 | 1.97 ± 1.2 |
| 8 | 4-acetyl-4-phenylpiperidine acyl | 2-thienyl | 2.48 mg/5.1% | 58.7 ± 0.8 | n/a- |
| 9 | 4-(carboxy)benzylamide | 2-thienyl | 2.78 mg/5.2% | 98.3 ± 1.1 | 0.66 ± 1.1 |
| 10 | 1-methanesulfonyl-spiro[indoline-piperidine] acyl | 2-thienyl | 16.26 mg/26.4% | 90.4 ± 0.5 | 1.23 ± 1.1 |
| 11 | 1-(2-oxo-benzimidazol-1-yl)piperidine acyl | 2-thienyl | 14.04 mg/47.6% | 90.4 ± 0.7 | 1.22 ± 1.4 |

TABLE 1-continued
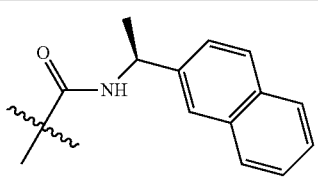 [SMILES: *C(=O)N[C@@H](C)c1ccc2ccccc2c1]
| Compound | R² | R¹ | Mass/yield | I[50] | IC50 (μM) |
|---|---|---|---|---|---|
| 12 | 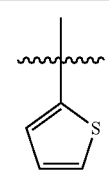 [SMILES: *c1cccs1] | 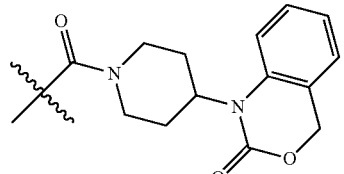 | 12.3 mg/14.5% | 99.8 ± 0.3 | 0.086 ± 1.1 |
| 13 | 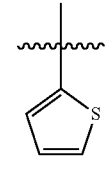 [SMILES: *c1cccs1] | 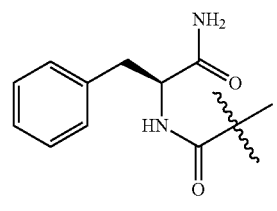 [SMILES: *C(=O)N[C@@H](Cc1ccccc1)C(N)=O] | 26.3 mg/43.2% | 87.9 ± 1.1 | 3.40 ± 1.4 |
| 14 | 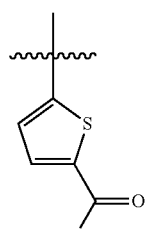 | 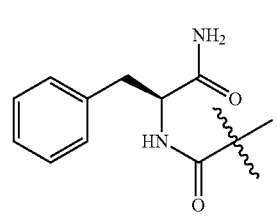 [SMILES: *C(=O)N[C@@H](Cc1ccccc1)C(N)=O] | 14.16 mg/16.6% | 83.4 ± 1.5 | 1.7 ± 1.8 |
| 15 | 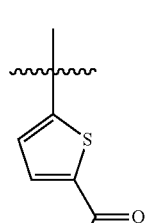 | 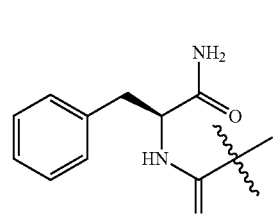 | 0.64 mg/0.7% | 19.4 ± 1.4 | — |
| 16 | 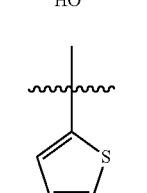 | 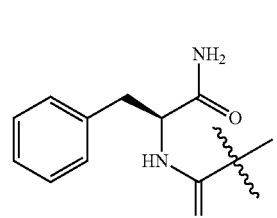 | 0.91 mg/1.8% | 89.4 ± 4.7 | 1.4 ± 1.3 |
| 17 | 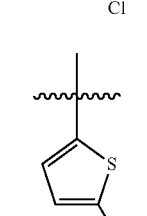 | | 1.7 mg/3.4% | 95.0 ± 1.1 | 2.0 ± 1.1 |

TABLE 1-continued

| Compound | R² | R¹ | Mass/yield | $I_{[50]}$ | $IC_{50}$ (μM) |
|---|---|---|---|---|---|
| 18 | phenylalaninamide | 5-acetylthiophen-2-yl | 1.34 mg/2.9% | 65.5 ± 7.7 | 5.1 ± 1.1 |
| 19 | phenylalaninamide | 3-chlorothiophen-2-yl | 0.42 mg/1% | 94.8 ± 2.4 | 3.2 ± 1.6 |
| 20 | phenylalaninamide | 5-cyanothiophen-2-yl | 0.46 mg/1% | 67.9 ± 1.6 | n/a |
| 21 | phenylalaninamide | 4-methylthiophen-2-yl | 0.54 mg/1.1% | 97.4 ± 0.8 | 0.38 ± 1.1 |
| 22 | phenylalaninamide | 3-methyl-5-cyanothiophen-2-yl | 0.46 mg/0.9% | 34.6 ± 2.1 | n/a |
| 23 | phenylalaninamide | 3-methylthiophen-2-yl | 1.08 mg/2.2% | 91.6 ± 0.8 | 1.87 ± 1.1 |

TABLE 1-continued

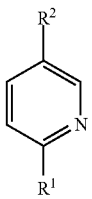

| Compound | R² | R¹ | Mass/yield | I[50] | IC50 (µM) |
|---|---|---|---|---|---|
| 24 | H₂N-CO-CH(CH₃)-NH-CO-CH(CH₂Ph)-NH-CO-CH(CH₃)-~ | 2-thienyl | | 94.6 ± 0.3 | 0.86 ± 1.2 |
| 25 | CH₃-CO-NH-CH(CH₃)-(2-naphthyl) | 4-methyl-2-thienyl | | 96.9 ± 1.0 | 0.18 ± 1.2 |

IC₅₀ values were calculated from triplicate experiments, and are presented as IC₅₀ ± Standard Error of the Mean. I[50] is percent inhibition at 50 µM, and is presented as the Mean ± Standard Error of triplicate experiments. '—' indicates that IC₅₀ values could not be retrieved under the assay conditions.

Effects of Selected H-PGDS Inhibitors on the Production of Other Prostaglandins, Prostacyclins and Thromboxanes A selection of compounds were assessed for their ability to inhibit inducible $PGD_2$ production in two inflammation-relevant cell models, mouse primary bone marrow-derived macrophages (BMM) responding to lipopolysaccharide (LPS), and the human megakaryocyte cell line, MEG-01S responding to PMA (Phorbol 12-myristate 13-acetate) differentiation, followed by triggering with the calcium ionophore A23187.

Cell Culture

All bone marrow-derived macrophages (BMM) were obtained by culturing bone marrow cells from the femurs of 6 to 8 week old C57BL/6 male mice in RPMI 1640 medium (Invitrogen Life Technologies, Carlsbad, Calif., USA) supplemented with 10% Fetal calf serum (Invitrogen) 20 U/ml penicillin and 20 µg/ml streptomycin (Invitrogen), 2 mM L-glutamine (Glutamax-1, Invitrogen) in the presence of $10^4$ U/ml (100 ng/mL) recombinant human CSF-1 (a gift from Chiron, Emeryville, Calif.) on bacteriological plastic plates for 7 days. The human megakaryocytic cell line MEG-01S was obtained from the American Type Culture Collection. MEG-01S were maintained in the same media as for BMM, supplemented with 1 mM Sodium Pyruvate (Invitrogen).

Determination of mRNA Expression by Quantitative PCR (qPCR)

As $PGD_2$ is produced by both H-PGDS and the genetically distinct L-PGDS, quantitative RT-PCR was first used to assess relative mRNA levels as an indicator of enzyme expression in these cell lines.

RNA was extracted from $3 \times 10^6$ cells and cDNA synthesised as described previously (Irvine, J Leuk Biol, 2009). Briefly, RNA was extracted using RNeasy kits (Qiagen, Valencia, Calif., USA), contaminating genomic DNA removed using RNeasy on-column DNase (Qiagen) and cDNA was synthesised using Superscript III (Invitrogen) and oligo(dT) primer. Transcript abundance was quantitated using gene-specific primer pairs and the SYBR green system (Applied Biosystems, Foster City, Calif., USA) relative to hypoxanthine guanine phosphoribosyl transferase (HPRT) levels using the power delta Ct method. Primer efficiencies for the respective human and mouse H-PGDS and L-PGDS primer pairs were measured over a cDNA dilution series, and were used to normalize expression, such that comparisons could be made of mRNA levels for H-PGDS versus L-PGDS (for human and mouse). Primer pairs used were Human H-PGDS gene, Human L-PGDS gene, Human HPRT gene, Mouse H-pgds gene, Mouse L-pgds gene and Mouse Hprt gene, as shown in Table 2.

TABLE 2

| Gene | Forward | Reverse |
|---|---|---|
| Human H-PGDS | TCACCAGAGCCTAGCAATAGCA | CTGCCCAAGGAAAACATGACA |
| Human L-PGDS | CCTGACCTCCACCTTCCTCA | TCGGTCTCCACCACTGACAC |
| Human HPRT | TCAGGCAGTATAATCCAAAGATGGT | AGTCTGGCTTATATCCAACACTTCC |
| Mouse H-pgds | AAGCACCTCGCCTTCTGAAA | CAGTAGAAGTCTGCCCAGGTTACAT |
| Mouse L-pgds | CAGAGGGCTGGTCACATGGT | AGGCAAAGCTGGAGGGTGTAG |
| Mouse Hprt | GCAGTACAGCCCCAAAATGG | AACAAAGTCTGGCCTGTATCCAA |

Results show that H-PGDS is the predominant PGDS expressed by mouse BMM and human MEG-01S cells.

Quantitative RT-PCR data from BMM and MEG-01S cells shows that H-PGDS mRNA was expressed at much higher levels (1000×) than L-PGDS in both mouse BMM and human MEG-01S cells.

BMM were treated with LPS over a time course and relative gene expression for H-PGDS and L-PGDS was quantitated. LPS was shown to induce L-PGDS expression in macrophages and H-PGDS was also regulated by LPS: Nonetheless, the increase in L-PGDS mRNA expression in response to LPS was very modest in comparison to the high basal expression of H-PGDS in BMM. It was concluded that H-PGDS is the major PGDS expressed by both human MEG-01S cells and mouse BMM, implying that this enzyme is likely to be the dominant source of $PGD_2$ production in these cell types.

Prostaglandin Release from Cells and Cell Viability:

Procedure: Prostaglandin Release from Cells

BMM were seeded overnight at $2\times10^5$ cells/ml in 24 well plates before treatment with compound at either 10 µM or 0.1-100 µM for 24 h in the presence or absence of lipopolysaccharide (LPS) from *Salmonella* Minnesota (Sigma-Aldrich) at a final concentration of 10 ng/ml. MEG-01S were seeded at $2\times10^5$ cells/ml and stimulated with PMA (Phorbol 12-myristate 13-acetate) (Sigma-Aldrich) at a final concentration of 0.1 µM for 16 h. Compound (0.3-100 µM) was added 30 min prior to stimulation with 5 µM Calcium Ionophore A23187 (Sigma-Aldrich) for 30 min. All compounds were dissolved in DMSO and diluted in cell culture medium such that the final concentration of DMSO did not exceed 0.1%. Supernatants were collected and samples were analysed for $PGD_2$ using Prostaglandin D2 Mox Express EIA kits, $PGE_2$ using Prostaglandin E2 Express EIA kits, the prostacyclin derivative 6-keto $PGF_{1\alpha}$ using the 6-keto Prostaglandin $F_{1\alpha}$ EIA Kit and the Thromboxane $A_2$ derivative $TXB_2$ using the Thromboxane $B_2$ Express EIA kit (Cayman Chemical) according to the manufacturer's instructions.

Procedure: Cell Viability Assays

Known inhibitors 1 and 2, along with compound 3, were used to treat BMM at three doses (10, 30, 100 µM) in the presence of LPS for 24 h and cell viability was measured by MTT assay. BMM were seeded at $1\times10^5$ cells/well in 96 well plates and treated for 24 h with LPS (10 ng/ml) and compounds at 10, 30 and 100 µM. MEG-01S were PMA differentiated overnight before compounds were added for a further 24 h at 10, 30 and 100 µM. Cell viability was measured by MTT (Sigma-Aldrich) assay as described previously (Irvine, FASEB J, 2006).

Prostaglandin $D_2$ Production in LPS-Activated BMMs

FIG. 1A shows the results of tests on compound 3 to assess its ability to inhibit $PGD_2$ production in LPS-activated BMMs. The compound was tested with 10 µM of compound and LPS (10 ng/ml) for 24 h. The average $PGD_2$ production from three independent experiments plus SEM is shown. * indicates p<0.05 versus LPS treatment alone. (Student's t test).

BMM Cell Viability

Compound 3 did not affect BMM viability at 10 µM or 100 µM, as assessed by MIT assay (FIG. 1B). Compounds 1 and 2, identified by others as H-PGDS inhibitors (Hohwy, 2008), had modest but significant effects on BMM cell viability (FIG. 1B). In FIG. 1B data show the average of four independent experiments plus SEM. * indicates p<0.05 versus control (one sample t test where the hypothetical mean is 100).

Prostaglandin Production in LPS-Activated BMMs: Compound 3

Compound 3 was further characterised along with the H-PGDS inhibitors 1 (HQL-79) (Aritake, 2006) and 2 (Hohwy, 2008) in LPS-activated BMM.

BMM were treated with increasing concentrations (0-100 µM) of compounds 1, 2 and 3 with appropriate vehicle controls (Ethanol for 1, DMSO for 3 and 2) and with LPS for 24 h. $PGD_2$ (FIG. 2A), $PGE_2$ (FIG. 2B) prostacyclin derivative 6-keto $PGF_{1\alpha}$ (FIG. 2C) and Thromboxane $A_2$ derivative $TXB_2$ (FIG. 2D) levels in supernatants collected from cells were quantified by EIA. Data show the average of three independent experiments plus SEM.* indicates p<0.05;  indicates p<0.01; * indicates p<0.001 (Student's t test) versus vehicle+LPS.

Figure 2:
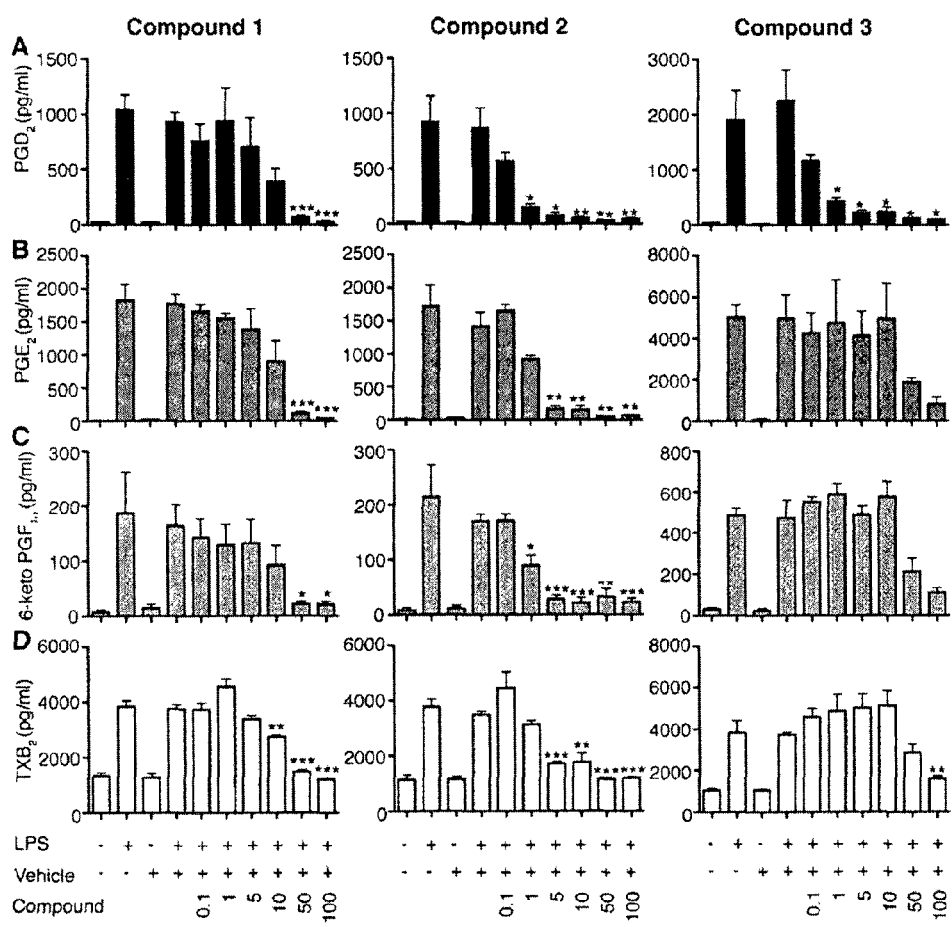
FIG. 2 depicts results from experiments to characterise compound 3 $PGD_2$ inhibition selectivity in mouse primary bone marrow-derived macrophages (BMM).

Compound 3 inhibited $PGD_2$ production in the sub-micromolar range dose-dependently (FIG. 2A). The $EC_{50}$ estimated for compound 3 (~0.29 µM) was comparable to that estimated for compound 2 ($EC_{50}$~0.16 µM), and was ~30 fold better than that estimated for 1. The specificities of 3, 2 and 1 were then assessed by comparing effects on LPS-inducible $PGE_2$, the hydrated prostacyclin derivative 6-keto $PGF_{1\alpha}$ and the thromboxane $A_2$ derivative TXB2 production from BMM (FIG. 2B). Compound 1 showed no differential effect in inhibition of $PGD_2$ versus $PGE_2$, 6-keto $PGF_{1\alpha}$ or $TXB_2$, while compound 2 showed only a modest difference. In contrast, compound 3 demonstrated a striking selectivity, significantly inhibiting $PGD_2$ levels at 1 µM, whilst $PGE_2$, 6-keto $PGF_{1\alpha}$ and $TXB_2$ inhibition was only observed above 10 µM. Taken together, these data demonstrate that compound 3 displays selectivity and affinity not otherwise observed for other H-PGDS inhibitors.

Figure 3:
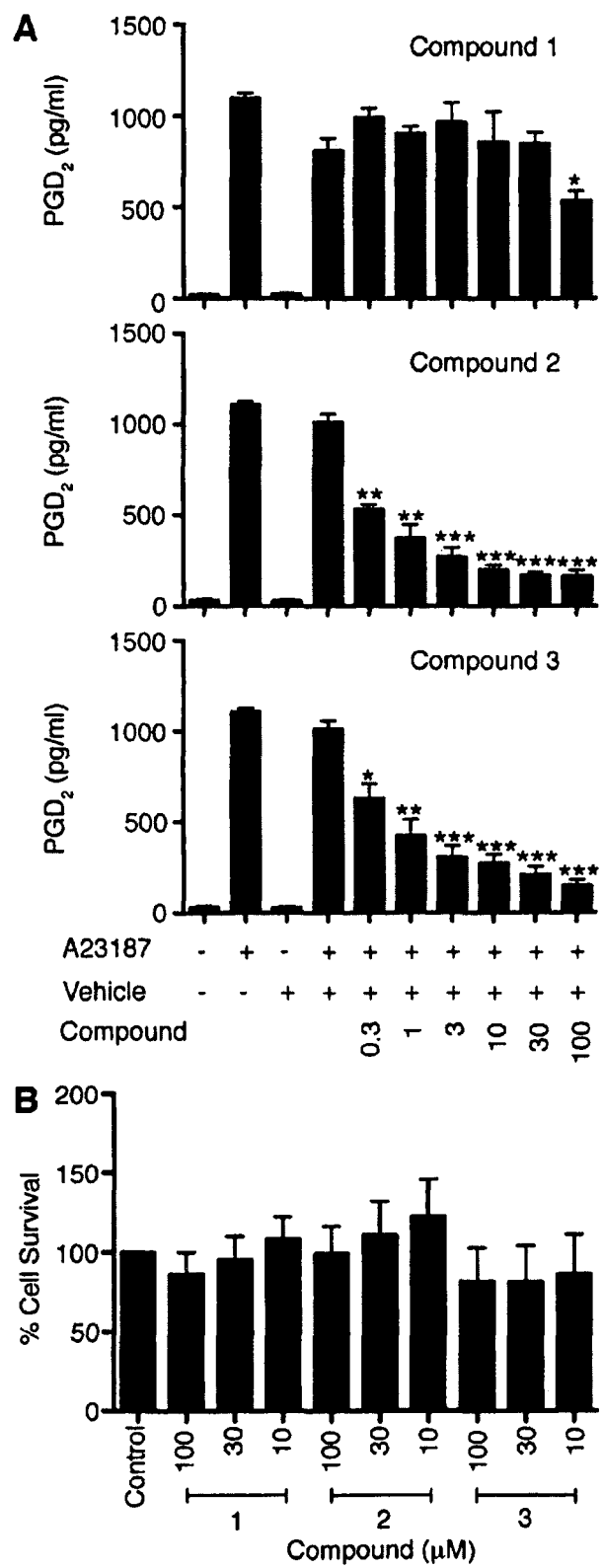
FIG. 3 shows results from experiments to characterise compound 3 $PGD_2$ inhibition in human megakaryocytes.

$PGD_2$ Inhibition in Human Megakaryocytes $PGD_2$ inhibition in human megakaryocytes by compound 3, and known inhibitors 1 and 2, were then characterised. PMA (Phorbol 12-myristate 13-acetate) differentiated MEG-01S were treated with compounds 1, 2 and 3 across a concentration range (0-100 µM) for 30 min prior to 30 minute treatment with 5 µM Calcium Ionophore A23187. $PGD_2$ levels in cell culture supernatants were quantitated by EIA (FIG. 3A). Data represent the average of three independent experiments plus SEM. * indicates p<0.05; indicates p<0.01; * indicates p<0.001 (Student's t test) versus vehicle+Ionophore.

Compounds 2 and 3 inhibited A23187-inducible $PGD_2$ production from PMA-differentiated MEG-01S human megakaryocytes dose-dependently, while 1 displayed very modest activity at 100 µM (FIG. 3A).

MEG-01S Cell Viability

The effect of the compounds on MEG-01S cell viability was measured by MTT assay after 24 h treatment across the concentration range 0-100 µM of compounds (FIG. 3B). Data represent the average of 4 independent experiments plus SEM.

Again, compound 3 had little effect on MEG-01S cell viability (FIG. 3B), as did compounds 1 and 2, suggesting that inhibition of $PGD_2$ production occurred through enzyme inhibition.

COX1 and COX2 Enzyme Assays

Figure 4:
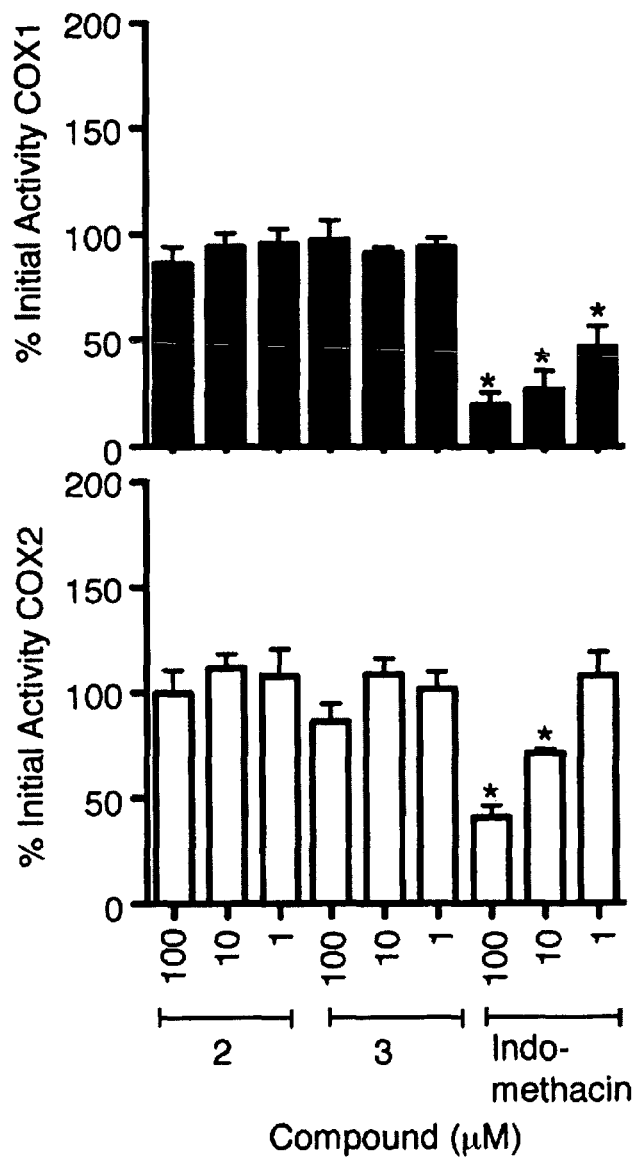
FIG. 4 shows results from experiments to characterise COX1 and COX2 inhibition by compound 3.

As inhibition of COX1 and/or 2 may also have a negative impact on $PGD_2$ production in cells, compound 3, along with known compound 2, was tested against purified COX1 and 2 isoforms at 1, 10 and 100 µM (FIG. 4). Tests were also performed on the well-characterized COX inhibitor, indomethacin, as a positive control. Data represent the average of three independent experiments plus SEM. * indicates p<0.05; (One sample t test where the hypothetical mean is 100).

COX1 and COX2 enzyme assays were performed using the Colorimetric COX (Ovine) Inhibitor Screening Assay kit (Cayman Chemical) according to the manufacturers instructions.

No inhibition of either COX isoform was observed for the H-PGDS inhibitors, whilst indomethacin significantly inhibited the activity of both COX1 and COX2 (FIG. 4). This data further supports the selectivity for $PGD_2$ synthesis inhibition of this series of compounds.

Pharmacokinetics and Rat Target Modulation assay

Male adult Sprague Dawley rates (~165 g) received a single oral bolus dose of 40 mg/kg of compound 3 in a 0.5% methylcellulose/0.1% Tween80 by oral gavage. Rats were sacrificed when collecting blood and spleen samples just prior to dosing and at 0.5 hours, 2 h, 8 h and 24 h (n=3 rats per time point), and the plasma concentration of compound 3 and the spleen $PGD_2$ concentration was measured at each time point.

Procedure: Blood Samples

Blood samples were removed and kept cold at approximately 4° C. immediately after collection to minimize degradation and centrifuged as soon as possible at approximately 4000×g for 10 min. The plasma was transferred to a clean, pre-labelled polypropylene tube and frozen. Samples were stored at −20° C. as soon as possible after collection to minimise degradation of the test item.

Plasma concentrations of 3 were determined using a screening LC-ms/ms method developed using the following parameters:

| Mobile Phase | A: 5% Acetonitrile/water, 0.1% TFA; B: 95% Acetonitrile/water, 0.09% TFA. Flow rate: 400 µl/min Gradient: 60% B for 0.5 min, up to 100% B in 1 min and remain at 100% B for a further 0.7 min. |
|---|---|
| Column | Phenomenex, Gemini C18, 150 × 2.0 mm, 5µ |
| Mass Spectrometer | 4000 Q TRAP |
| Polarity | positive |
| Transition | m/z 353/307 and 352/161 |

Samples were analysed alongside plasma standards. Concentration data were determined by back calculation from standard curve.

Procedure: Spleen Samples

Spleens were excised, weighed and snap frozen in a dry ice/ethanol bath. Tissues were stored at −80° C. until analysis. Spleens were homogenised in a solution containing 10 mM indomethacin in phosphate buffered saline (PBS) at 1:10 w/v. Samples were centrifuged at 2500 rpm for 5 min at 4° C. The resultant supernatant was diluted and the measurement of $PGD_2$ was determined by solid-phase extraction (SPE) using cationic solid-phase extraction cartridges. The SPE eluent was assayed using a screening LC-MS/MS method against aqueous $PGD_2$ standards, using the following LC-MS/MS parameters:

| Mobile Phase | A: 10 mM Ammonium acetate, pH 8.5; B: 95% Acetonitrile/water. Flow rate: 200 µl/min Gradient: Linear from 20% B to 50% B in 10 min |
|---|---|
| Column | Phenomenex, Luna Phenyl-hexyl, 3µ, 150 × 2.0 mm |
| Mass Spectrometer | 4000 Q TRAP |
| Polarity | negative |
| Transition | m/z 351/271 |

Results

The observed levels of compound 3 in rat serum after oral dosing is illustrated in Table 3. Compound 3 was orally bioavailable and present in the serum 8 hours post delivery. Compound 3 also showed reduction in $PGD_2$ activity, 20% at the 8 hour time point.

TABLE 3

| Time (h) | Concentration (ng/mL) | N | Mean (± sem) Concentration (ng/mL) |
|---|---|---|---|
| 0 | BLOQ[1] | 3 | 0 |
| 0 | BLOQ[1] | | |
| 0 | BLOQ[1] | | |
| 0.5 | 177 | 3 | 219 ± 24.8 |
| 0.5 | 263 | | |
| 0.5 | 218 | | |
| 2 | 94.8 | 3 | 91.8 ± 9.79 |
| 2 | 73.5 | | |
| 2 | 107 | | |
| 8 | 17.3 | 3 | 44.3 ± 14.0 |
| 8 | 63.9 | | |
| 8 | 51.8 | | |
| 24 | BLOQ[2] | 3 | 0.677 ± 0.177 |
| 24 | 1.03 | | |
| 24 | BLOQ[2] | | |

Entries marked BLOQ were Below the Lower Limit of Quantitation.
BLOQ[1] - treated as 0 in calculating the mean.
BLOQ[2] - treated as 0.5 ng/mL (1/2 lower limit of quantitation) in calculating the mean.

REFERENCES

K. Aritake et al., Structural and Functional Characterization of HQL-79, an Orally Selective Inhibitor of Human Hematopoietic Prostglandin D Synthase, J. Biol. Chem. 2006, 281:15277-15286.

M. M. Bradford et al., A rapid and sensitive method for the quantitation of microgram quantities of protein utilizing the principle of protein-dye binding, Anal. Biochem, 1976, 72:248-254.

T. W. Green and P. G. M. Wuts, Protective Groups in Organic Synthesis, John Wiley & Sons, 3rd Edition 1999.

M. Hohwy et al., Novel Prostaglandin D Synthase Inhibitors Generated by Fragment-Based Drug Design, J. Med. Chem., 2008, 51:2178-2186.

I. R. Jowsey et al., Mammalian class Sigma glutathione S-transferases: catalytic properties and tissue-specific expression of human and rat GSH-dependent prostaglandin D2 synthases, Biochem. J., 2001, 359:507-516.

K. M. Irvine et al., A CSF-1 receptor kinase inhibitor targets effector functions and inhibits pro-inflammatory cytokine production from murine macrophage populations, FASEB J, 2006, 20:1921-1923.

K. M. Irvine et al., Colony-stimulating factor-1 (CSF-1) delivers a proatherogenic signal to human macrophages, J. Leukoc. Biol., 2009, 85:278-288.

The invention claimed is:

1. A compound of formula (III) or a pharmaceutically acceptable salt thereof:

Formula (III)

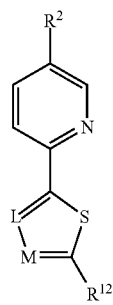

wherein
- L and M are both $CR^{13}$;
- $R^2$ is $-C(=O)-NR^3R^4$;
- $R^3$ is $-CHR^8R^{11}$;
- $R^4$ is selected from hydrogen, hydroxyl, alkyl, haloalkyl, alkenyl, and alkynyl;
- $R^8$ is selected from $-CO_2H$, $-CONH_2$, cycloalkyl, cycloalkenyl, aryl, heterocyclyl, heteroaryl, $-C_{1-6}$alkyl$R^{10}$, $-C_{2-6}$alkenyl$R^{10}$ and $-C_{2-6}$alkynyl$R^{10}$;
- $R^{10}$ is selected from cycloalkyl, cycloalkenyl, aryl, heterocyclyl and heteroaryl;
- $R^{11}$ is selected from $-C_{2-6}$alkyl, $-C_{1-6}$haloalkyl, $-C_{2-6}$alkenyl, $-C_{2-6}$alkynyl, $-C_{0-6}$alkylOH, $-C_{0-6}$alkylCO$_2$H, $-C_{0-6}$alkylCONH$_2$, $-C_{0-6}$alkylNH$_2$, $-C_{0-6}$alkylSH, $-C_{0-6}$alkylSC$_{1-6}$alkyl, $-C_{0-6}$alkyl-NHC(=NH)NH$_2$, $-C_{0-6}$alkylcycloalkyl, $-C_{0-6}$alkylaryl, $-C_{0-6}$alkylheterocyclyl and $-C_{0-6}$alkylheteroaryl;
- $R^{12}$ and $R^{13}$ are independently selected from hydrogen, cyano, nitro, halo, $-C_{1-6}$alkyl, $-C_{2-6}$alkenyl, $-C_{2-6}$alkynyl, $-C_{0-6}$alkylaryl, $-C_{0-6}$alkylheteroaryl, $-C_{0-6}$alkylcycloalkyl, $-C_{0-6}$alkylcycloalkenyl, $-C_{0-6}$alkylheterocyclyl, $-O-R^{14}$, $-C(=O)-R^{14}$, $-C(=O)-O-R^{14}$, $-O-C(=O)-R^{14}$, $-S(O)_t-R^{14}$, $-N(R^{14})_2$, and $-C(=O)-N(R^{14})_2$, wherein each $R^{14}$ is independently selected from H, $-C_{1-6}$alkyl, $-C_{2-6}$alkenyl, $-C_{2-6}$alkynyl, $-C_{0-6}$alkylaryl, $-C_{0-6}$alkylheteroaryl, $-C_{0-6}$alkylcycloalkyl, $-C_{0-6}$alkylcycloalkenyl or $-C_{0-6}$alkylheterocyclyl; and
- t is 0-2;

wherein each alkyl, alkenyl, alkynyl, cycloalkyl, cycloalkenyl, aryl, heterocyclyl and heteroaryl are optionally substituted with one or more optional substituents.

2. The compound according to claim 1 wherein each $R^{13}$ is independently selected from hydrogen, cyano, nitro, halo, $-C_{1-6}$alkyl, $-C_{2-6}$alkenyl, $-C_{2-6}$alkynyl, $-C(=O)-R^{14}$, $-C(=O)-O-R^{14}$, $-O-C(=O)-R^{14}$, $-N(R^{14})_2$, and $-C(=O)-N(R^{14})_2$.

3. The compound according to claim 1, wherein at least one of L and M is CH.

4. The compound according to claim 1, wherein L and M are both CH.

5. The compound according to claim 1, wherein $R^{12}$ is hydrogen, cyano, nitro, halo, $-C_{1-6}$alkyl, $-C_{2-6}$alkenyl, $-C_{2-6}$alkynyl, $-C(=O)-R^{14}$, $-C(=O)-O-R^{14}$, $-O-C(=O)-R^{14}$, $-N(R^{14})_2$, and $-C(=O)-N(R^{14})_2$.

6. The compound according to claim 5, wherein $R^{12}$ is selected from hydrogen, cyano, nitro, halo, $-C_{1-6}$alkyl, $-C(=O)-R^{14}$, $-C(=O)-O-R^{14}$ or $-O-C(=O)-R^{14}$, where $R^{14}$ is hydrogen or $C_{1-6}$alkyl.

7. The compound according to claim 5, wherein $R^{12}$ is hydrogen.

8. The compound according to claim 1, wherein $R^8$ is $-CONH_2$ or optionally substituted aryl.

9. The compound according to claim 1, wherein $R^{11}$ is $-C_{2-6}$alkyl, $-C_{1-6}$perfluoroalkyl or $-C_{0-6}$alkylaryl.

10. The compound according to claim 1, wherein $R^4$ is hydrogen.

11. A pharmaceutical composition comprising a compound according to claim 1 and at least one pharmaceutically acceptable carrier.

* * * * *